(12) United States Patent
Seo et al.

(10) Patent No.: US 10,167,465 B2
(45) Date of Patent: Jan. 1, 2019

(54) METHOD OF DIFFERENTIATING ADULT STEM CELLS INTO NERVE CELLS BY USING HIGH-INTENSITY ELECTROMAGNETIC FIELD

(71) Applicant: DONGGUK UNIVERSITY INDUSTRY-ACADEMIC COOPERATION FOUNDATION, Jung gu, Seoul (KR)

(72) Inventors: Young Kwon Seo, Seongdong-gu (KR); Jung Keug Park, Seodaemun-gu (KR); Hee Hun Yoon, Bucheon-si (KR); Hyun Jin Cho, Seocho-gu (KR); Hee Jung Park, Seongbuk-gu (KR); Yu Mi Kim, Songpa-gu (KR); Bo-Young Yoo, Gangdong-gu (KR); Sang Eun Cho, Yangju-si (KR); Sang Heon Kim, Bupyeong-gu (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 99 days.

(21) Appl. No.: 15/301,355

(22) PCT Filed: Apr. 2, 2015

(86) PCT No.: PCT/KR2015/003306
§ 371 (c)(1),
(2) Date: Sep. 30, 2016

(87) PCT Pub. No.: WO2015/152656
PCT Pub. Date: Oct. 8, 2015

(65) Prior Publication Data
US 2017/0152500 A1    Jun. 1, 2017

(30) Foreign Application Priority Data

Apr. 2, 2014   (KR) ........................ 10-2014-0039150
Apr. 2, 2015   (KR) ........................ 10-2015-0046741

(51) Int. Cl.
*C12N 13/00*    (2006.01)
*C12N 5/079*    (2010.01)

(52) U.S. Cl.
CPC ........... *C12N 13/00* (2013.01); *C12N 5/0622* (2013.01); *C12N 2506/1346* (2013.01); *C12N 2506/1353* (2013.01); *C12N 2529/00* (2013.01)

(58) Field of Classification Search
CPC .. A61K 45/06; A61K 31/7105; A61K 31/713; A61K 49/0067; A61K 9/0009; A61K 9/0048; A61K 9/5115; A61K 31/58; A61K 48/00; A61K 48/0033; A61K 48/0083; A61K 41/0042; A61K 48/0058; A61K 9/1611; A61K 31/485; A61K 41/00; A61K 47/6901; A61K 49/1896; C12N 13/00; C12N 2506/1346; C12N 2506/1353; C12N 2529/00; C12N 2506/1361; C12N 2506/1369; C12N 2506/1384; C12N 5/0618; C12N 5/0619; C12N 5/0622

See application file for complete search history.

(56) References Cited

U.S. PATENT DOCUMENTS

| | | | | |
|---|---|---|---|---|
| 8,469,034 | B2 * | 6/2013 | Dobson | A61K 41/00 128/898 |
| 8,673,605 | B2 * | 3/2014 | Park | C12N 13/00 435/173.1 |
| 2005/0075679 | A1 | 4/2005 | Gliner et al. | |
| 2006/0205993 | A1 | 9/2006 | Fischell et al. | |
| 2007/0065941 | A1 | 3/2007 | Kondo et al. | |
| 2011/0034753 | A1 * | 2/2011 | Dobson | A61K 41/00 600/12 |
| 2013/0202565 | A1 * | 8/2013 | Park | C12N 13/00 424/93.7 |

FOREIGN PATENT DOCUMENTS

| | | |
|---|---|---|
| JP | 2008-543388 A | 12/2008 |
| KR | 10-1210998 B1 | 12/2012 |

OTHER PUBLICATIONS

Meng, D., et al. "The effects of high-intensity pulsed electromagnetic field on proliferation and differentiation of neural stem cells of neonatal rats in vitro", J Huazhoug Univ Sci Technol, Dec. 2009, vol. 29, No. 6, pp. 732-736, published online on Dec. 29, 2009.
Park, J-E et al., "Electromagnetic fields induce neural differentiation of human bone marrow derived mesenchymal stem cells via ROS mediated EGFR activation", Neurochemistry International, 2013, vol. 62, p. 418-424, Published online on Feb. 11, 2013.
Cho, H. et al., "Neural stimulation on human bone marrow-derived mesenchymal stem cells by extremely low requency electromagnetic fields", Biotechnology Progress, 2012, vol. 28, No. 5, pp. 1329-1335, Published online on Sep. 18, 2012.
ISA/KR, International Search Report dated Jul. 10, 2015 in International Application No. PCT/KR2015/003306, total 9 pages with English translation.
Ahmadian, Shahin et al., "Effects of extremely-low-frequency pulsed electromagnetic fileds on collagen synthesis in rat skin", Biotechnol Appl. Biochem., 2006, vol. 43, p. 71-75.
Ceccarelli, Gabriele et al., "A Comparative Analysis of the In Vitro Effects of Pulsed Electromagnetic Field Treatment on Osteogenic Differentiation of Two Different Mesenchymal Cell Lineages", BioResearch Open Access, vol. 2, No. 4, p. 283-294, Aug. 2013.

(Continued)

*Primary Examiner* — Deborah K Ware
(74) *Attorney, Agent, or Firm* — Masuvalley & Partners

(57) ABSTRACT

The present invention provides methods of differentiating mesenchymal stem cells or adult stem cells into nerve cells by treating the mesenchymal stem cells or the adult stem cells with an electromagnetic field having a high intensity of 100 to 1,500 mT and a low frequency of 0.01 to 100 Hz. These methods also provide injecting the mesenchymal stem cells or adult stem cells into a subject prior to treating the mesenchymal stem cells or adult stem cells with an electromagnetic field having a high intensity of 100 to 1,500 mT and a low frequency of 0.01 to 100 Hz.

8 Claims, 23 Drawing Sheets

(56) References Cited

OTHER PUBLICATIONS

Datta, Abhishek et al., "Cranial electrotherapy stimulation and transcranial pulsed current stimulation: A computer based high-resolution modeling study", NeuroImage, vol. 65, pp. 280-287, Journal homepage: www.elsevier.com/locate/ynimg.

Schwartz, Z. et al., "Pulsed Electromagnetic Fields Enhance BMP-2 Dependent Osteoblastic Differentiation of Human Mesenchymal Stem Cells", Journal of Orthopaedic Research, Sep. 2008, Published online in Wiley InterScience (www.interscience.wiley.com). DOI 10.1002/jor.20591, p. 1250-1255.

\* cited by examiner

METHOD OF DIFFERENTIATING ADULT STEM CELLS INTO NERVE CELLS BY USING HIGH-INTENSITY ELECTROMAGNETIC FIELD

TECHNICAL FIELD

The present invention relates to a method of differentiating mesenchymal stem cells or adult stem cells into nerve cells. More particularly, the present invention relates to a method of differentiating mesenchymal stem cells or adult stem cells into nerve cells by treating the corresponding stem cells with a high-intensity electromagnetic field.

BACKGROUND ART

Various studies showing that the differentiation of stem cells is promoted using an electromagnetic field have been reported. Fregni et al. reported that various types of electric and electromagnetic field stimulation relieve pain from chronic neuralgia caused by spinal damage (Non-patent Document 1), and Ahmadian S. et al. reported that an increase in the collagen of mouse skin is observed when the skin of mice is irradiated daily with a frequency of 25 Hz and an intensity of 2 mT for 2.5 hours (Non-patent Document 2).

Also, studies on osteogenesis using an electromagnetic field have been reported. Ceccarelli et al. reported that the osteogenic differentiation of various mesenchymal stem cells is promoted by an electromagnetic field having a frequency of 75 Hz and an intensity of 2 mT (Non-patent Document 3), Sun et al. reported that, when bone marrow-derived mesenchymal stem cells are cultured under an electromagnetic field having a frequency of 15 Hz and an intensity of 1.8 mT, the expression of alkaline phosphatase (ALP) and a bone morphogenetic protein (BMP-2) is promoted to stimulate the differentiation into osteocytes, and Schwartz et al. reported that the osteogenic differentiation of mesenchymal stem cells is promoted by an electromagnetic field having a frequency of 15 Hz and an intensity of 1.6 mT. The study on the promotion of osteogenic differentiation using such an electromagnetic field uses an electromagnetic field having a frequency of 7.5 to 15 Hz and an intensity of 0.1 to 5 mT (Non-patent Document 4).

In recent years, as therapeutic methods using stem cells to treat neurological diseases such as Alzheimer's disease, depression, Parkinson's disease, cerebral infarction, cerebral hemorrhage, damaged spinal cord and the like have emerged, methods using electrical stimulation in research conducted to promote the differentiation into nerve cells have also been reported. As the neurotherapeutic techniques known in the related art, there is a device configured to apply energy with a low frequency of approximately 10 Hz or less to brain tissue, characterized in that, after electrodes are implanted into a patient's brain, electrical stimulation is directly applied to the electrodes to induce a magnetic field using a flow of electricity (Patent Document 1). Zheng developed a method of applying magnetic stimulation to the central nervous system as a technique in which high frequencies or a plurality of frequency components are combined and used to improve brain functions (Patent Document 2), and Riken developed a technique of treating embryonic stem cells with electric pulses to prepare nerve cells (Patent Document 3). Gliner et al. developed a technique of treating cells with electric pulses to prepare nerve cells (Patent Document 4). The above-described methods have limits on clinical applications since an additional surgical operation in which electrodes are implanted using a method of directly implanting electrodes should be conducted, thereby inflicting pain on patients and increasing the likelihood of embryonic stem cells forming tumors. Therefore, there is a demand for novel technology for differentiating mesenchymal stem cells and adult stem cells into nerve cells using a non-invasive method rather than a chemical method. Because of such a demand, the present inventors have conducted research on the mesenchymal stem cells and the adult stem cells as cell therapy products for treating various neuron-associated diseases. Therefore, the present invention has been completed based on these facts.

PRIOR-ART DOCUMENTS

Non-Patent Documents

1. Fregni et al., Cranial electrotherapy stimulation and transcranial pulsed current stimulation: A computer based high-resolution modeling study, NeuroImage, Volume 65, Pages 280-287, 15 Jan. 2013.
2. Ahmadian S et al., Effects of extremely-low-frequency pulsed electromagnetic fields on collagen synthesis in rat skin, Biotechnol. Appl. Biochem. 2006, 43, 71-75.
3. Ceccarelli et al., A Comparative Analysis of the In Vitro Effects of Pulsed Electromagnetic Field Treatment on Osteogenic Differentiation of Two Different Mesenchymal Cell Lineages, BioResearch Open Access, 2013, 2(4): 283-294.
4. Schwartz Z, Simon B J, Duran M A, Barabino G, Chaudhri R, Boyan B D. Pulsed electromagnetic fields enhance BMP-2 dependent osteoblastic differentiation of human mesenchymal stem cells. J Orthop Res. 2008; 26(9):1250-1255.

Patent Documents

1. US Patent Laid-Open Publication No. 2006-0205993
2. Japanese Patent Laid-Open Publication No. 2008-543388
3. US Patent Laid-Open Publication No. 2007-0065941
4. US Patent Laid-Open Publication No. 2005-0075679

DISCLOSURE

Technical Problem

The present invention is directed to providing a method of differentiating mesenchymal stem cells or adult stem cells into nerve cells, which includes treating the mesenchymal stem cells or the adult stem cells with a high-intensity electromagnetic field.

Also, the present invention is directed to providing a medical device to which the method is applied.

Technical Solution

The present invention is directed to providing a method of differentiating mesenchymal stem cells or adult stem cells into nerve cells, which includes treating the mesenchymal stem cells or the adult stem cells with an electromagnetic field having a high intensity of 100 to 1,500 mT.

The term "electromagnetic field" used in this specification refers to a state in which an electromagnetic field having a periodically varying intensity propagates into space, and thus has the same meanings as electronic waves. Here, the electromagnetic field used in the present invention may include both types of pulsed waves and continuous waves (sine waves).

The term "high intensity" used in this specification means that an electromagnetic field has an intensity of 10 mT or more. In the present invention, stem cells may be preferably treated with an electromagnetic field having a high intensity of 10 to 1,500 mT, 100 to 1,500 mT, 200 to 1,500 mT, 300 to 1,500 mT, 400 to 1,500 mT, and most preferably 500 to 1,500 mT. When the high intensity of the electromagnetic field is out of this range, conversion efficiency of the stem cells into nerve cells may be degraded.

Also, the electromagnetic field of the present invention may form low-frequency electronic waves having a frequency of 0.01 to 1000 Hz, preferably 1 to 100 Hz, 40 Hz to 80 Hz, 50 Hz to 80 Hz, most preferably 60 Hz to 80 Hz, and particularly preferably 60 Hz to 75 Hz. When the frequency of the low-frequency electronic waves is out of this range, conversion efficiency of the stem cells into nerve cells may be degraded.

The term "electronic wave" used in this specification refers to a state in which an electromagnetic field having a periodically varying intensity propagates into space, and thus has the same meanings as electromagnetic waves. Here, the low-frequency electronic waves refer to waves having a low frequency, generally a frequency of 10 kHz or less.

According to one exemplary embodiment of the present invention, it was confirmed that an amount of nerve cell-associated proteins increases when adult stem cells are cultured using an electromagnetic field under conditions of a high intensity and a low frequency. In particular, it was confirmed that, when the adult stem cells are cultured using an electromagnetic field under conditions of a low frequency of 45 Hz to 85 Hz and a high intensity of 100 to 1,500 mT, the neuron-associated proteins in the adult stem cells are expressed to the highest level. Therefore, it can be seen that, when the method of the present invention is applied, the adult stem cells may differentiate into nerve cells (FIG. 7).

In the present invention, the adult stem cells may be treated with the electromagnetic field for 1 to 60 min/day over 3 to 20 days, preferably treated for 5 to 30 min/day over 3 to 15 days, and most preferably for 15 to 20 min/day over 5 to 15 days.

The term "stem cells" refer to undifferentiated cells that can divide for a long period of time, renew themselves (self-renewal), and differentiate into various types of cells when the cells are under certain conditions. The stem cells are classified into embryonic stem cells and adult stem cells, depending on which tissues the stem cells are derived from. The neural stem cells may be classified into an intermediate phase between the embryonic stem cells and the adult stem cells, and are known to be able to be induced to differentiate into desired cells such as nerve cells in a relative easy manner. On the other hand, the adult stem cells are known to have no side effects, compared to the embryonic stem cells, but are known to be difficult to be induced to differentiate into desired cells.

The "adult stem cells" may also include the mesenchymal stem cells, and the adult stem cells may include periodontal ligament cells, dental pulp stem cells, bone marrow-derived mesenchymal stem cells, umbilical cord-derived mesenchymal stem cells, adipose tissue-derived mesenchymal stem cells, etc. Preferably, among the adult stem cells, the periodontal ligament cells, the dental pulp stem cells, or the neural progenitor cells may be differentiated into nerve cells by culturing these adult stem cells using an electromagnetic field having a certain frequency and a high intensity. As the adult stem cells, commercially available stem cells, or stem cells isolated from biological tissues may be used without limitation.

The term "nerve cells" used in this specification may include all of Schwann cells, astrocytes, oligodendrocytes, and neurons. Here, the nerve cells differentiated by the method of the present invention may include astrocytes or oligodendrocytes.

According to one exemplary embodiment of the present invention, to check an effect of inducing the differentiation of the adult stem cells when treated with the electromagnetic field having a high intensity and a low frequency, expression levels of MMP 1, Neuro D1, and NF-L are determined through immunohistochemical staining. As a result, it can be seen that the expression of Neuro D1, NF-L proteins as nerve cell indicators increases in all groups in which the stem cells are treated with the high-intensity/low-frequency electromagnetic field of the present invention, compared to the group in which the stem cells are not treated with the low-intensity electromagnetic field, indicating that the nerve regeneration most actively occurs. That is, it can be seen that, since the neuronal proteins are most strongly expressed in the cultured adult stem cells, the differentiation of the adult stem cells into nerve cells is actively induced when the adult stem cells are treated for 15 to 20 min/day with the electromagnetic field of the present invention having a low frequency of 45 Hz to 75 Hz and a high intensity of 100 to 1,500 mT (FIGS. 12, 13 and 14).

Also, the present invention is directed to providing a composition for treating damaged nerve tissue using the method. Here, the composition includes differentiated nerve cells. Proper stem cells may be administered into the body through the composition using a conventional method. In this case, the stem cells may be included at a therapeutically effective amount required to maximize a therapeutic effect when the stem cells are administered once or several times. The cells may be prepared to be mixed with an injectable solution immediately before use. In this case, physiological saline, glucose, mannitol, Ringer's solution and the like may be used as the injectable solution.

The damaged nerve tissue may originate from one or more diseases selected from the group consisting of Alzheimer's disease, depression, Parkinson's disease, cerebral infarction, cerebral hemorrhage, a damaged spinal cord, and a damaged peripheral nerve, preferably originating from a neurological disease. The differentiated nerve cells or neural stem cells according to the present invention may serve to recover the functions of the nerve cells in the neurological disease, and thus may be used as the composition for treating a neurological disease.

Also, the present invention is directed to providing a medical device to which the method is applied.

In addition, the present invention is directed to providing a medical device including the nerve cells differentiated by the method. The medical device may be used to treat damaged nerve tissue. The damaged nerve tissue may originate from one or more diseases selected from the group consisting of Alzheimer's disease, depression, Parkinson's disease, cerebral infarction, cerebral hemorrhage, a damaged spinal cord, and a damaged peripheral nerve, preferably originating from a neurological disease. The differentiated nerve cells or neural stem cells according to the present invention may serve to recover the functions of the nerve cells in the neurological disease, and thus may be used as one component of the medical device.

Additionally, the present invention is directed to providing a method of differentiating mesenchymal stem cells or adult stem cells into nerve cells, which includes injecting the mesenchymal stem cells or the adult stem cells into a subject, and treating the mesenchymal stem cells or the adult stem cells with an electromagnetic field having a high intensity of 100 to 1,500 mT.

A vertebrate including a human, preferably a mammal, and more preferably a human, non-human anthropoids, cattle, a pig, a rodent (a mouse or a rat), a rabbit, a guinea pig, a hamster, a dog, or a cat may be used as the subject, but the present invention is not limited thereto.

Also, the mesenchymal stem cells or the adult stem cells may include stem cells which are injected into the body of the subject, more preferably a brain of the subject, and most preferably damaged nerve tissue of the subject. According to one exemplary embodiment of the present invention, after the human mesenchymal stem cells are injected into a rat stroke model, the rat stroke model is treated with a low-intensity electromagnetic field (EMF) and a high-intensity electromagnetic field (h-EMF), and tissues are then collected and subjected to Western blotting. As a result, it can be seen that the expression of the neuron-associated proteins MAP 2 and Neuro D1 increases, indicating that the increased expression of the neuron-associated proteins is caused due to an increase in p-ERK and p-CREB. The immunostaining results show that the expression of MMP is reduced in the groups in which the stem cells are treated with the high-intensity electromagnetic field, resulting in reduced inflammation (FIG. 12), and that the Neuro D1 and NF-L proteins are strongly stained in the groups (60 Hz, 630 mT, and 20 min/day) in which the stem cells are treated with the high-intensity electromagnetic field, compared to the groups (60 Hz, 1 mT, and 60 min/day) in which the stem cells are treated with the low-intensity electromagnetic field, indicating that the nerve regeneration more actively occurs.

Also, in the present invention, after the undifferentiated mesenchymal stem cells or differentiated nerve cells are injected into the body, an affected part may be treated with a high-intensity electromagnetic field daily for 20 minutes to maximize therapeutic efficiency in the damaged nerve tissue.

Also, the electromagnetic field applied to the method of the present invention may form low-frequency electronic waves having a frequency of 0.01 to 1000 Hz, preferably 1 to 100 Hz, and most preferably a frequency of 45 Hz to 75 Hz. When the frequency of the low-frequency electronic waves is out of this range, conversion efficiency of the stem cells into nerve cells may be degraded. In the present invention, the adult stem cells may be treated with the electromagnetic field for 1 to 60 min/day over 3 to 20 days, preferably treated for 5 to 30 min/day over 3 to 15 days, and most preferably for 15 to 20 min/day over 5 to 15 days. The nerve cells may include astrocytes or oligodendrocytes, and the "adult stem cells" may also include the mesenchymal stem cells, and the adult stem cells may include periodontal ligament cells, dental pulp stem cells, bone marrow-derived mesenchymal stem cells, umbilical cord-derived mesenchymal stem cells, and adipose tissue-derived mesenchymal stem cells. Preferably, among the adult stem cells, the periodontal ligament cells, the dental pulp stem cells, or the neural progenitor cells may be cultured using an electromagnetic field having a certain frequency and a high intensity to differentiate into nerve cells. As the adult stem cells, commercially available stem cells, or stem cells isolated from biological tissues may be used without limitation. Also, the nerve cells may include all of Schwann cells, astrocytes, oligodendrocytes, and neurons, and the nerve cells differentiated by the method of the present invention may include astrocytes or oligodendrocytes.

Further, the present invention is directed to providing a medical device to which the method is applied. The medical device may be used to treat damaged nerve tissue. The damaged nerve tissue may originate from one or more diseases selected from the group consisting of Alzheimer's disease, depression, Parkinson's disease, cerebral infarction, cerebral hemorrhage, a damaged spinal cord, and a damaged peripheral nerve, preferably originating from a neurological disease. The differentiated nerve cells or neural stem cells according to the present invention may serve to recover the functions of the nerve cells in the neurological disease, and thus may be used as one component of the medical device.

Advantageous Effects

The method and the composition for differentiation into stem cells using a magnetic field according to the present invention can induce the differentiation of adult stem cells into nerve cells using a low-frequency/high-intensity electromagnetic field so that the adult stem cells may be easily differentiated into nerve cells or neural stem cells only when the adult stem cells are treated with the electromagnetic field for a short time. Also, the stem cells differentiated by the method can be effectively used to treat neurological diseases such as Alzheimer's disease, depression, Parkinson's disease, cerebral infarction, cerebral hemorrhage, a damaged spinal cord, and a damaged peripheral nerve.

BEST MODE

Hereinafter, the present invention will be described in detail.

The present invention relates to a system for regeneration of damaged nerves, and a method of promoting differentiation of mesenchymal stem cells or adult stem cells into neuron-associated cells. Specifically, the present invention relates to a system for promoting differentiation into neuron-like cells through in vivo physical stimulation or promoting regeneration of damaged neurons with stem cells injected into the body. More specifically, the present invention relates to a system for promoting differentiation of mesenchymal stem cells or adult stem cells into neuron-like cells by exposing the mesenchymal stem cells or adult stem cells to a certain low-frequency/high-intensity electromagnetic field, or a system for promoting recovery of damaged nerve tissue by injecting mesenchymal stem cells or adult stem cells into the body and exposing the mesenchymal stem cells or adult stem cells to a low-frequency/high-intensity electromagnetic field. The present invention relates to a system capable of improving the established differentiation efficiency of an electromagnetic field by applying a high-intensity electromagnetic field to mesenchymal stem cells or adult stem cells for a short time. The electromagnetic field of the present invention can differentiate mesenchymal stem cells or adult stem cells into nerve cells only when the mesenchymal stem cells or the adult stem cells are treated with certain frequencies. Therefore, the present inventors have ensured a technique of inducing in vitro neuronal differentiation of adult stem cells using a high-intensity electromagnetic field according to the present invention.

Figure 1:
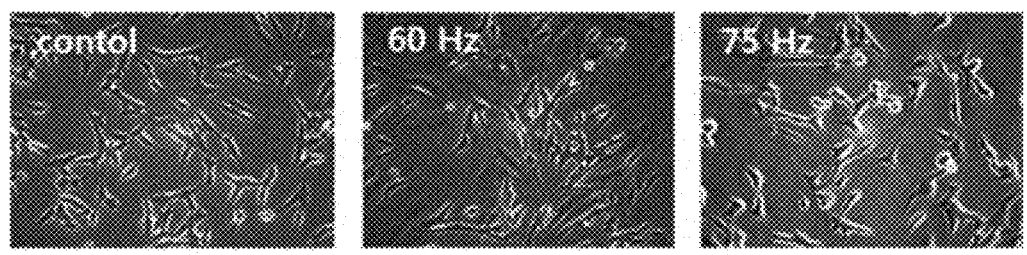
FIG. 1 shows morphological results using neural progenitor cells after treatment with a high-intensity electromagnetic field according to one exemplary embodiment of the present invention (Control: untreated group; and 60 Hz and 75 Hz: treated with frequencies of the high-intensity electromagnetic field).
Figure 2:
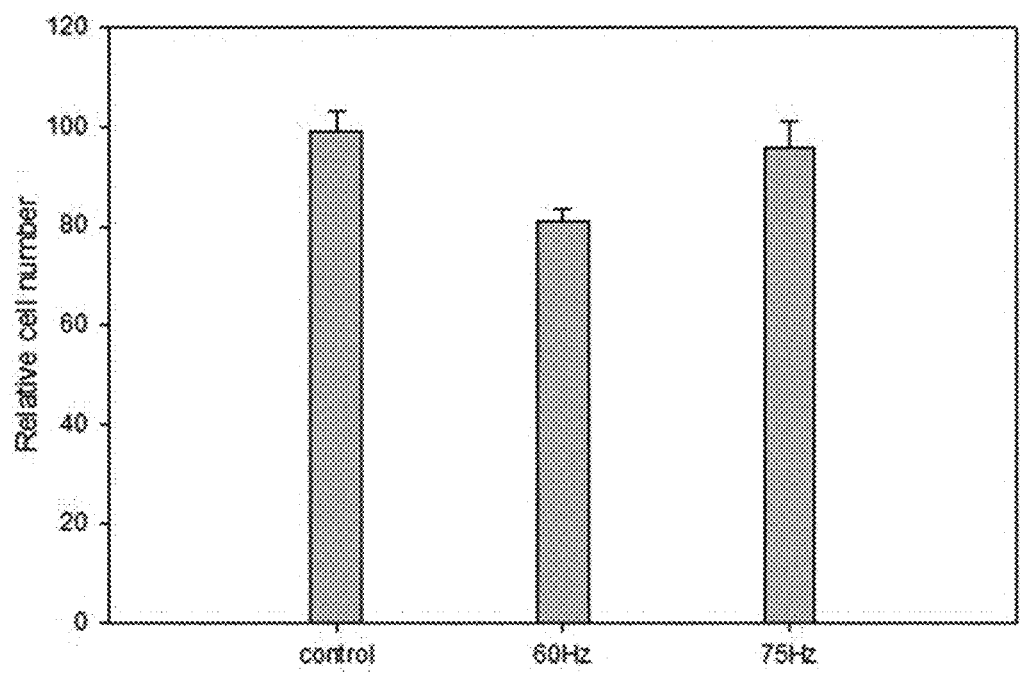
FIG. 2 shows results of determining viability of neural progenitor cells after treatment with a high-intensity electromagnetic field according to one exemplary embodiment of the present invention (Control: untreated group; and 60 Hz and 75 Hz: treated with frequencies of the high-intensity electromagnetic field).
Figure 3:
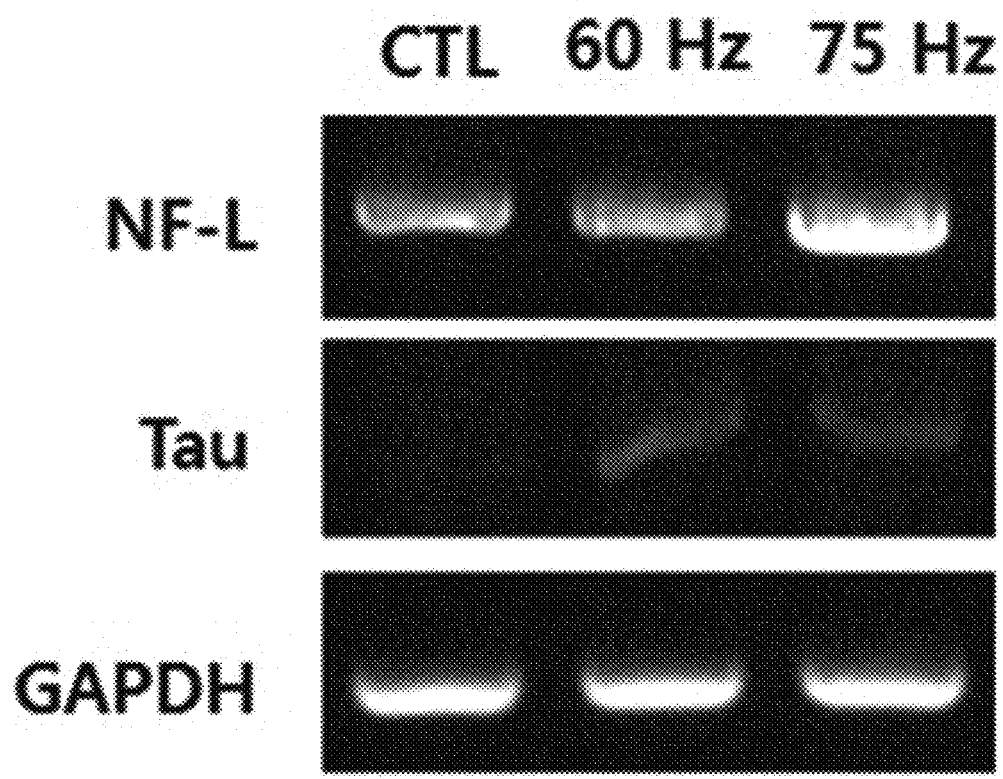
FIG. 3 shows results of expression of neuronal differentiation-associated mRNAs after treatment with a high-intensity electromagnetic field according to one exemplary embodiment of the present invention (CTL: untreated group; and 60 Hz and 75 Hz: treated with frequencies of the high-intensity electromagnetic field).
Figure 4:
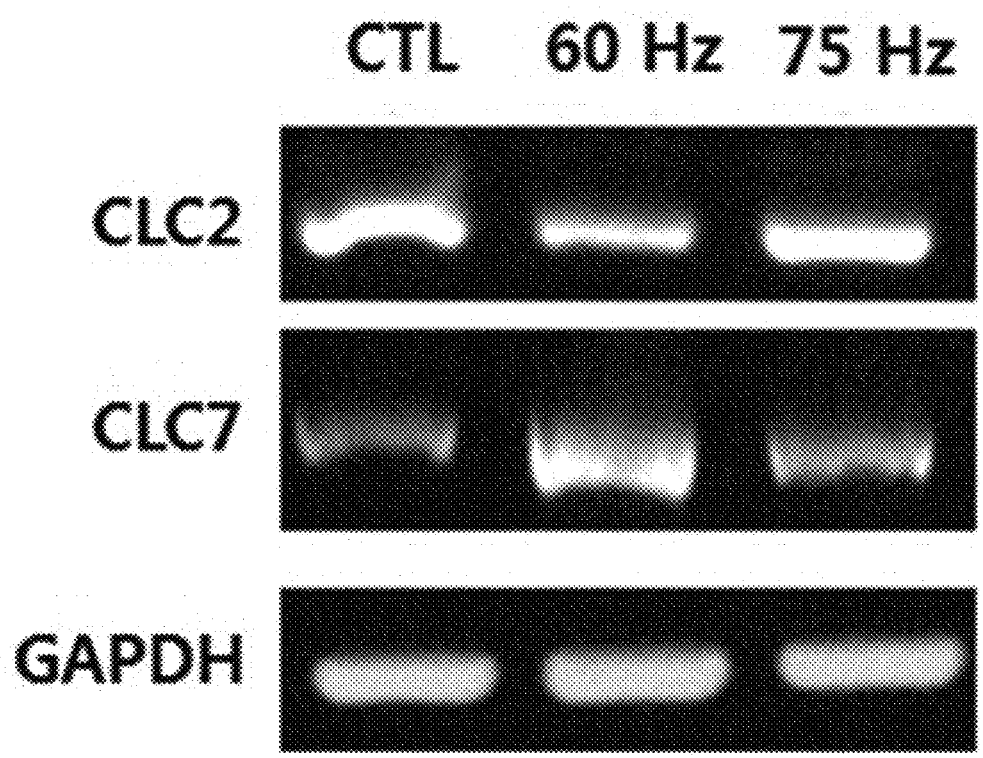
FIG. 4 shows results of mRNA expression of chloride channel-associated factors CLC2 and CLC7, which are associated with electrophysiological signaling, after treatment with a high-intensity electromagnetic field according to one exemplary embodiment of the present invention (CTL: untreated group; and 60 Hz and 75 Hz: treated with frequencies of the high-intensity electromagnetic field).

According to one exemplary embodiment of the present invention, it is confirmed that, when SH-SY5Y neural progenitor cells are treated with a high-intensity electromagnetic field daily for 20 minutes over 5 days, the length of dendrites increases at frequencies of 60 Hz and 75 Hz to improve the differentiation of the neural progenitor cells, as shown in FIG. 1. In this case, the analysis results of cell viability show that the treatment with the high-intensity electromagnetic field does not have a significant effect on cell viability (FIG. 2). FIG. 3 shows analysis results of expression of neuron-associated neurofilament (NF) and Tau mRNAs. Here, it is confirmed that the neuron-associated proteins are increasingly expressed, compared to the group in which the stem cells are not treated with an electromagnetic field (FIG. 3). FIG. 4 shows that such a high-intensity electromagnetic field activates chloride channels (CLCs) to promote differentiation.

Figure 5:
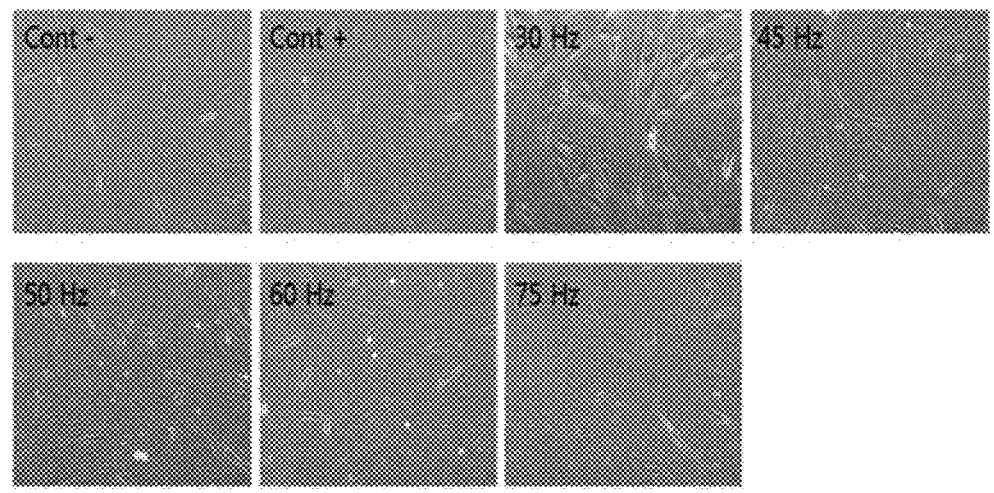
FIG. 5 shows results of determining morphological changes of adult stem cells after the adult stem cells are treated with a high-intensity electromagnetic field in vitro to induce neuronal differentiation of the adult stem cells in an experiment conducted under conditions used to induce the neuronal differentiation of the adult stem cells according to one exemplary embodiment of the present invention. A growth medium is used in Cont−, and a medium for inducing the neuronal differentiation (hereinafter referred to as a differentiation medium) is used in Cont+, 30 Hz, 45 Hz, 50 Hz, 60 Hz, and 70 Hz (75H???). The intensities of the high-intensity electromagnetic field are set to 30 Hz (1,120 mT), 45 Hz (890 mT), 50 Hz (680 mT), 60 Hz (630 mT), and 70 Hz (570 mT) (Cont−: an untreated group using a growth medium; Cont+: an untreated group using a differentiation medium; and 30 Hz, 45 Hz, 50 Hz, 60 Hz, and 75 Hz: treated with frequencies of the high-intensity electromagnetic field).
Figure 6:
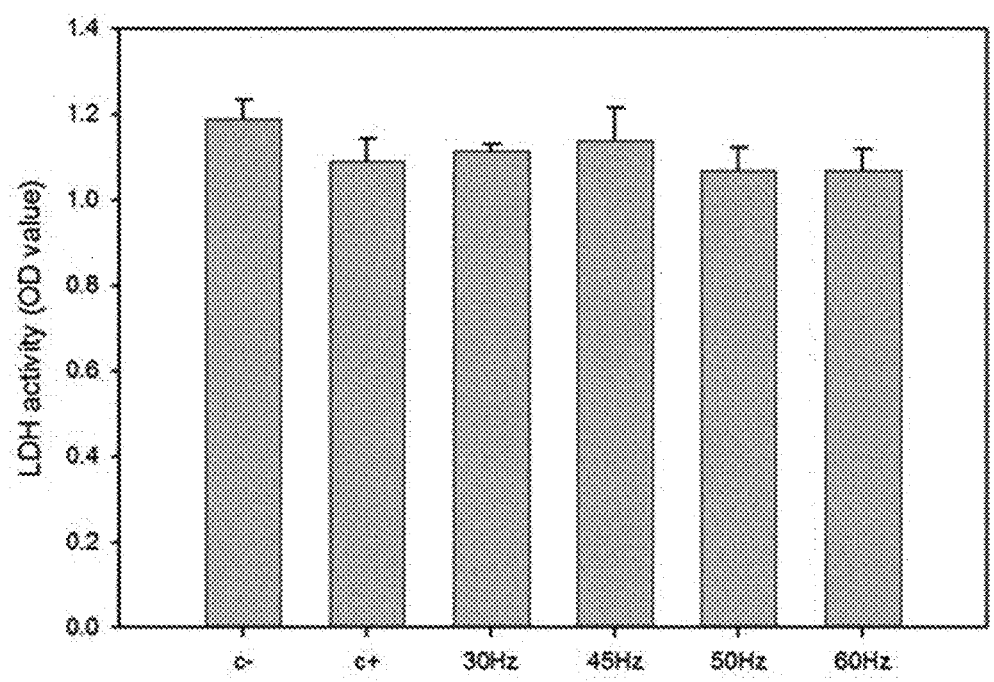
FIG. 6 shows lactate dehydrogenase (LDH) assay results of determining that LDH is secreted from adult stem cells after the adult stem cells are treated with a high-intensity electromagnetic field to induce the neuronal differentiation of the adult stem cells according to one exemplary embodiment of the present invention (C−: an untreated group using a growth medium; C+: an untreated group using a differentiation medium; and 30 Hz, 45 Hz, 50 Hz, and 60 Hz: treated with frequencies of the high-intensity electromagnetic field).
Figure 7:
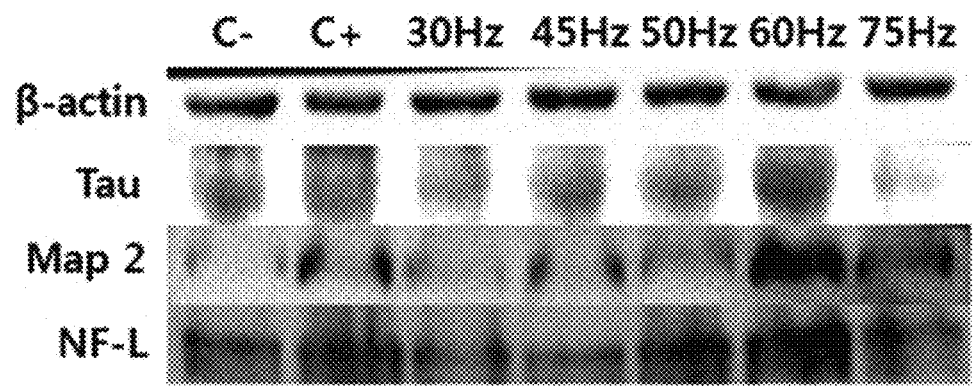
FIG. 7 shows results of comparing expression levels of neuron-associated proteins after adult stem cells are treated with a high-intensity electromagnetic field to induce the neuronal differentiation of the adult stem cells according to one exemplary embodiment of the present invention (C−: an untreated group using a growth medium; C+: an untreated group using a differentiation medium; and 30 Hz, 45 Hz, 50 Hz, 60 Hz, and 75 Hz: treated with frequencies of the high-intensity electromagnetic field).

According to one exemplary embodiment of the present invention, the neuronal differentiation of mesenchymal stem cells is induced for 8 days by treatment with high-intensity/low-frequency electromagnetic waves, and observed under a microscope (FIG. 5). As a result, it is confirmed that the cell death (apoptosis) and the like are not observed even at various frequencies. Also, the LDH assay results show that no damage to cell membranes is caused, as shown in FIG. 6. On the other hand, it is confirmed that, when mesenchymal stem cells are exposed to a high-intensity electromagnetic field having a frequency of 30 Hz, 45 Hz, 50 Hz, 60 Hz, and 70 Hz, the expression of the neuron-associated proteins MAP2, Tau, NF-L increases, indicating that the neuronal differentiation of the mesenchymal stem cells at 60 Hz is improved (FIG. 7).

Figure 12:
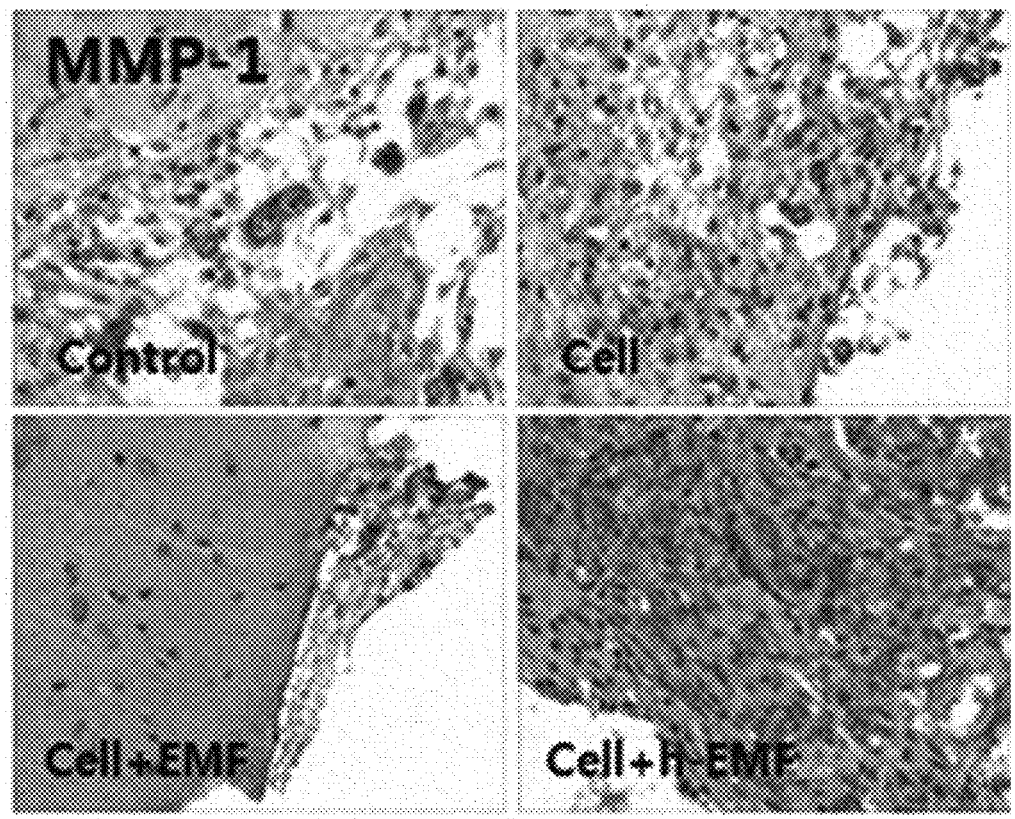
FIG. 12 shows results of expression of a nerve cell-associated factor MMP 1 after a small animal stroke model is established and adult stem cells are then injected and treated with a high-intensity electromagnetic field according to one exemplary embodiment of the present invention (Control: control group; Cell: an adult stem cell-administered group; Cell+EMF: an adult stem cell-administered/low-intensity electromagnetic field-treated group; and Cell+h-EMF: an adult stem cell-administered/high-intensity electromagnetic field-treated group).
Figure 13:
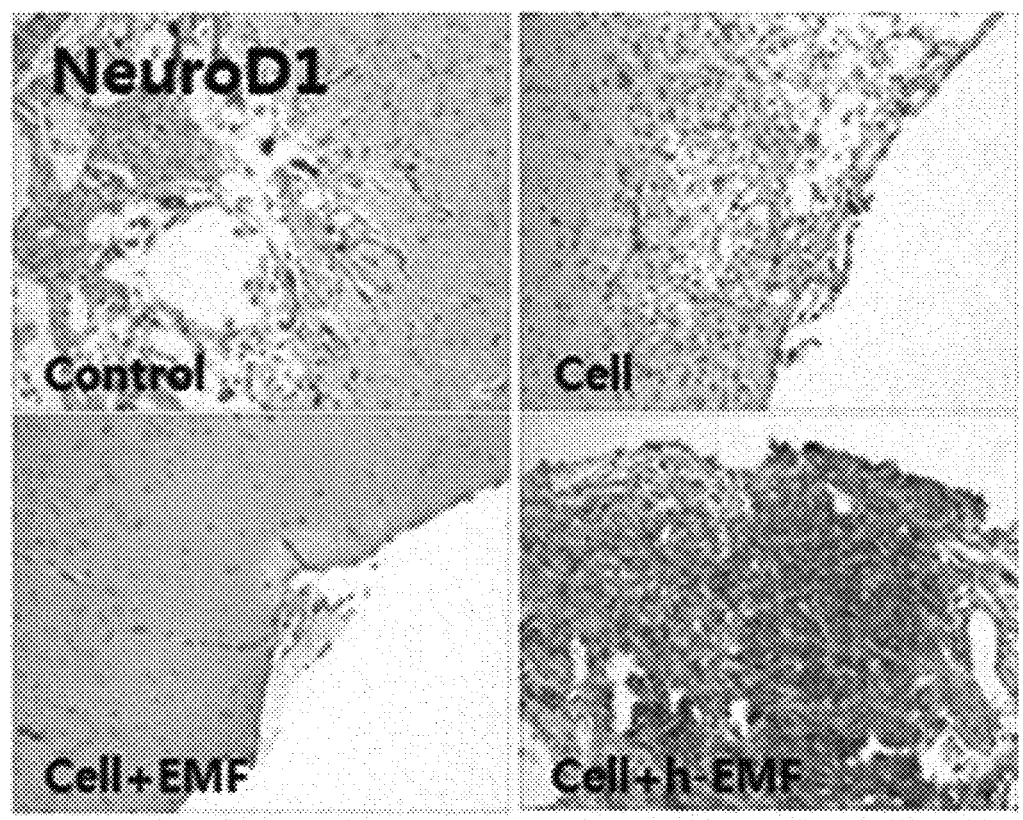
FIG. 13 shows results of expression of a nerve cell-associated factor Neuro D1 after a small animal stroke model is established and adult stem cells are then injected and treated with a high-intensity electromagnetic field according to one exemplary embodiment of the present invention (Control: control group; Cell: an adult stem cell-administered group; Cell+EMF: an adult stem cell-administered/low-intensity electromagnetic field-treated group; and Cell+h-EMF: an adult stem cell-administered/high-intensity electromagnetic field-treated group).
Figure 14:
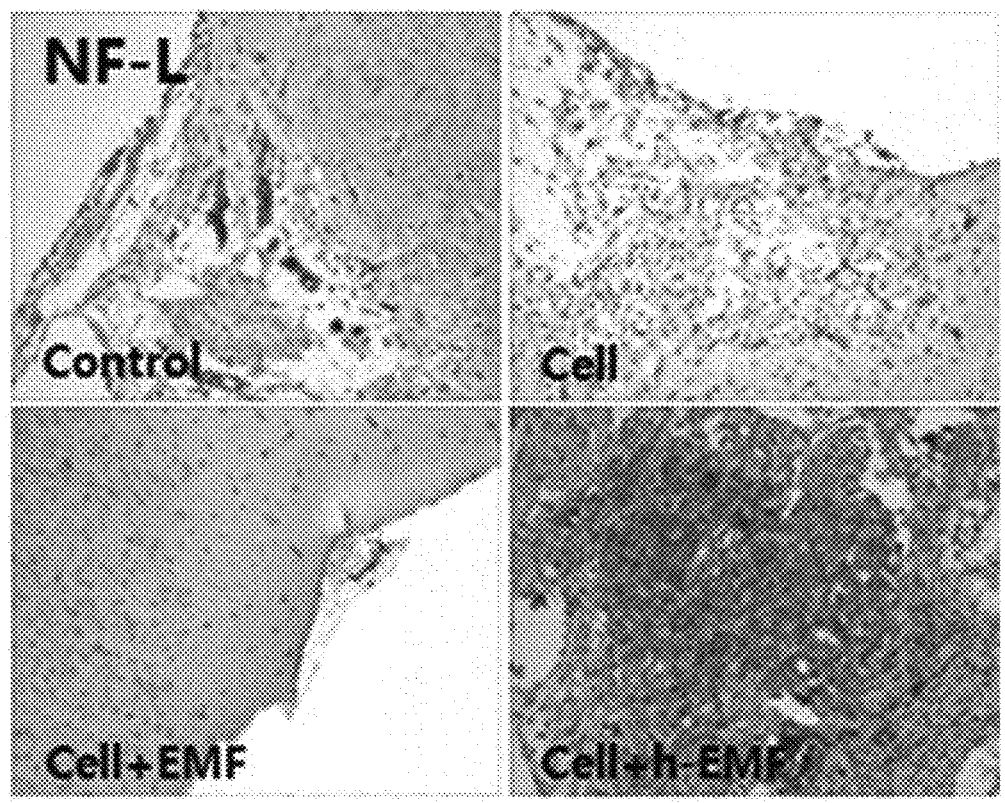
FIG. 14 shows results of expression of a nerve cell-associated factor NF-L after a small animal stroke model is established and adult stem cells are then injected and treated with a high-intensity electromagnetic field according to one exemplary embodiment of the present invention (Control: control group; Cell: an adult stem cell-administered group; Cell+EMF: an adult stem cell-administered/low-intensity electromagnetic field-treated group; and Cell+h-EMF: an adult stem cell-administered/high-intensity electromagnetic field-treated group).

Also, according to one exemplary embodiment of the present invention, human mesenchymal stem cells are injected into a rat stroke model, and treated with a low-intensity electromagnetic field (EMF) and a high-intensity electromagnetic field (h-EMF), and tissue is collected and subjected to Western blotting. As a result, it is confirmed that the expression of the neuron-associated proteins MAP 2 and Neuro D1 increases, indicating that the increased expression of the neuron-associated proteins is caused due to an increase in p-ERK and p-CREB. The immunostaining results show that the expression of MMP in the high-intensity electromagnetic field-treated group is reduced, resulting in decreased inflammation (FIG. 12), and that Neuro D1 and NF-L are strongly stained in the high-intensity electromagnetic field-treated group (at 60 Hz and 630 mT for 20 min/day), compared to the low-intensity electromagnetic field-treated group (at 60 Hz and 1 mT for 60 min/day), as shown in FIGS. 13 and 14, indicating that the nerve regeneration more actively occurs.

Also, in the present invention, after the undifferentiated mesenchymal stem cells or differentiated nerve cells are injected into the body, an affected part may be treated with a high-intensity electromagnetic field daily for 20 minutes to maximize therapeutic efficiency in the damaged nerve tissue.

MODE FOR INVENTION

Hereinafter, the present invention will be described in further detail with reference to examples thereof. However, it should be understood that the following examples provided herein are merely intended to provide a better understanding of the present invention and are not intended to limit the scope of the present invention.

Example 1: Effect of High-Intensity Electromagnetic Field on Differentiation of Nerve Cells Using Nerve Cell Line

Example 1.1: Culturing of Nerve Cell Line

An SH-SY5Y neural progenitor cell line (Catalog No. CRL-2266) was purchased from the American Type Culture Collection (ATCC), and cultured in a DMEM medium supplemented with 5% (v/v) FBS and 5 µM retinoic acid. The cell line was seeded in a culture plate, and then cultured in a $CO_2$ incubator maintained at a constant temperature of 37° C. while the medium was replaced with a fresh one every three days.

Example 1.2: Confirmation of Differentiation of Neural Progenitor Cell Line Using High-Intensity Electromagnetic Field The cultured neural progenitor cells were seeded in a 12-well plate at a concentration $2 \times 10^4$ cells/well, and cultured in a $CO_2$ incubator at 37° C. for 5 days while the medium was replaced with a fresh one every three days.

The treatment with the high-intensity electromagnetic field was performed twice daily for 15 minutes over a culture period. Here, the treatment was performed while a culture plate was placed over a high-intensity electromagnetic field. The neural progenitor cells were cultured for 5 days under an electromagnetic field having a frequency of 0 Hz (an untreated group), 60 Hz (at 630 mT) and 75 Hz (at 570 mT), and then cultured in a DMEM medium supplemented with 5% (v/v) FBS and 5 µM retinoic acid. After the culturing, the neural progenitor cells were observed under an optical microscope to check a morphological change of the neural progenitor cells. The results are shown in FIG. 1.

As shown in FIG. 1, it was revealed that dendrites tended to extend from the neural progenitor cell line cultured using the electromagnetic field in the treated groups, compared to the untreated group.

Also, FIG. 2 shows the number of cells observed to evaluate the viability of the nerve cells after treatment with a high-intensity electromagnetic field. It was revealed that the treatment with the high-intensity electromagnetic field had no effect on cell viability in all the treated groups (60 Hz (at 630 mT) and 75 Hz (at 570 mT)), compared to the untreated group.

In addition, FIG. 3 shows results of observing expression of neuronal differentiation-associated mRNAs after treatment with a high-intensity electromagnetic field. It was observed that the expression of NF-L and Tau increased in the 60 Hz- and 75 Hz-treated groups, compared to the untreated group.

Further, FIG. 4 shows results of comparing mRNA expression levels of chloride channel-associated factors CLC2 and CLC7, which are associated with electrophysiological signaling, after treatment with a high-intensity electromagnetic field. As a result, it was revealed that the CLC2 and CLC7 were strongly expressed in the 60 Hz- and 75 Hz-treated groups.

Example 2: Culturing of Adult Stem Cells Using High-Intensity Electromagnetic Field

Example 2.1: Primary Culturing of Adult Stem Cells

Human adult stem cells whose passage number was 2 were purchased from Lonza (Walkersville, Md.), put into an NH medium, and then centrifuged at 800 rpm for 5 minutes. A supernatant obtained by the centrifugation was discarded, and the remaining cells were again seeded in a 100 mm culture plate containing 10 ml of an NH medium, and then cultured in a $CO_2$ incubator maintained at a constant temperature of 37° C. while the medium was replaced with a fresh one every three days.

Example 2.2: Confirmation of Differentiation of Adult Stem Cells Cultured Using High-Intensity Electromagnetic Field into Nerve Cells After the primary culturing, the medium was removed, and the cultured cells were washed with 10 ml of phosphate buffered saline (PBS) one or more times. 1 ml of a solution containing 0.05% (w/v) trypsin and 0.01% (w/v) EDTA was added to the washed cells, and the cells were treated at 37° C. for 5 minutes so that the cells were detached from the bottom of the culture plate to float in the solution. The cell solution was mixed with 15 ml of an NH medium containing 10% (v/v) FBS, and the mixture was then centrifuged at 800 rpm for 5 minutes to discard a supernatant and collect the cells. The collected cells were sub-cultured up to five times in a $CO_2$ incubator.

The cultured cells were seeded in a DMEM medium-containing 60 mm culture plate at a concentration of $0.25 \times 10^5$ cells/culture plate, and then cultured in a $CO_2$ incubator at 37° C. for 8 days while the medium was replaced with a fresh one every three days. In this case, the experimental groups were treated with a high-intensity electromagnetic field.

The treatment with the high-intensity electromagnetic field was performed once daily for 20 minutes over a culture period. When the treatment was performed, the 60 mm culture plate was placed over the high-intensity electromagnetic field, and the cells were then cultured for 7 days under the electromagnetic field having a frequency of 0 Hz (an untreated group), 30 Hz (at 1,120 mT), 45 Hz (at 890 mT), 50 Hz (at 680 mT), 60 Hz (at 630 mT), and 70 Hz (at 570 mT). The cells were cultured in a DMEM medium supplemented with 5% FBS, 10 ng/ml EGF, and 10 µM Forskolin. After the culturing, the adult stem cells were observed under an optical microscope to determine morphological changes of the adult stem cells at 0 Hz (an untreated group), 30 Hz (at 1,120 mT), 45 Hz (at 890 mT), 50 Hz (at 680 mT), 60 Hz (at 630 mT), and 70 Hz (at 570 mT). The results are shown in FIG. 5.

As shown in FIG. 5, it could be seen that apoptosis-associated behavior such as vacuole formation or cell membrane collapse were not observed in the adult stem cells cultured using the electromagnetic field, indicating that the frequencies and intensities used in this study did not cause toxicity to the cells.

Also, a lactate dehydrogenase (LDH) assay was carried out to evaluate an effect of the high-intensity electromagnetic field on cytotoxicity. The results are shown in FIG. 6. As shown in FIG. 6, the LDH assay is an analysis method of evaluating a stress state of cells by determining whether LDH is secreted when cells are under stress or cell membranes are damaged. Since there was no significant difference in optical density (OD) values between the groups in which the stem cells were treated and were not treated with the high-intensity electromagnetic field even when grown under all the conditions, it could be seen that the high-intensity electromagnetic field did not cause stress to the cells or damage to the cell membranes.

Also, the cells were cultured and collected to analyze expression levels of the nerve cell-associated proteins Tau, MAP 2, and Neuro D1. As shown in FIG. 7, an amount of the nerve cell-associated proteins increased in the adult stem cells cultured using the high-intensity electromagnetic field. In particular, the neuron-associated proteins were expressed to the highest level in the adult stem cells cultured under the electromagnetic field having a frequency of 60 Hz (at 630 mT). Therefore, it can be seen that the adult stem cells were differentiated into nerve cells.

Figure 8:
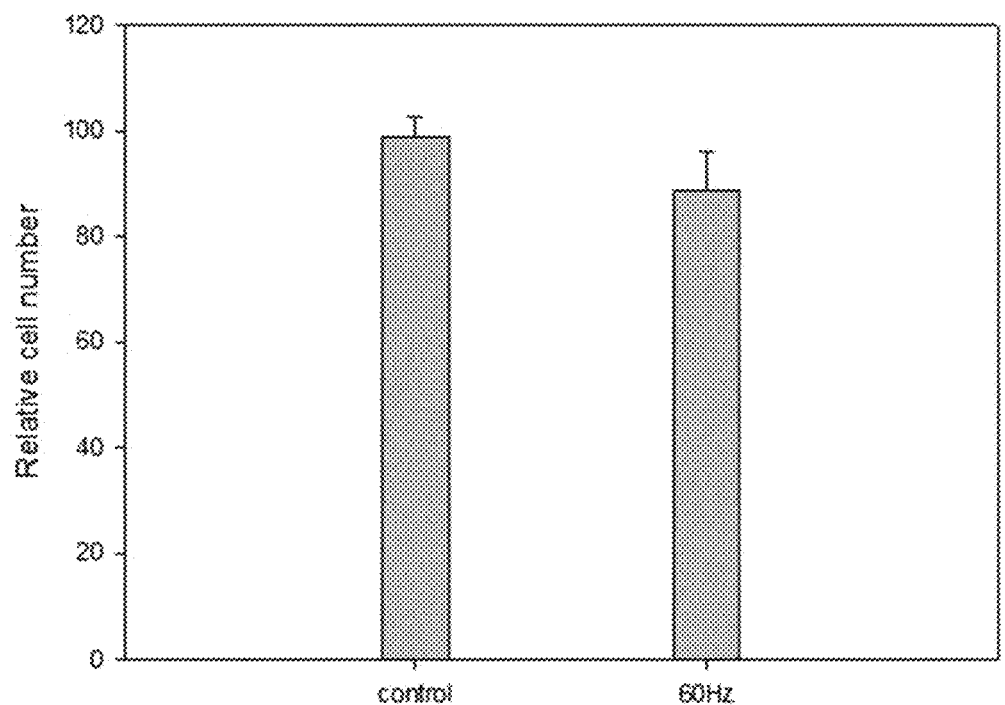
FIG. 8 shows viability results of adult stem cells after treatment with a high-intensity electromagnetic field in order to perform an animal efficacy assay according to one exemplary embodiment of the present invention (Control: untreated group; and 60 Hz: treated with a frequency of the high-intensity electromagnetic field).

Further, the in vitro viability of the adult stem cells at 60 Hz was analyzed to evaluate in order to perform an animal efficacy assay (FIG. 8). As a result, it could be seen that the electromagnetic field had no effect on cell viability.

Figure 9:
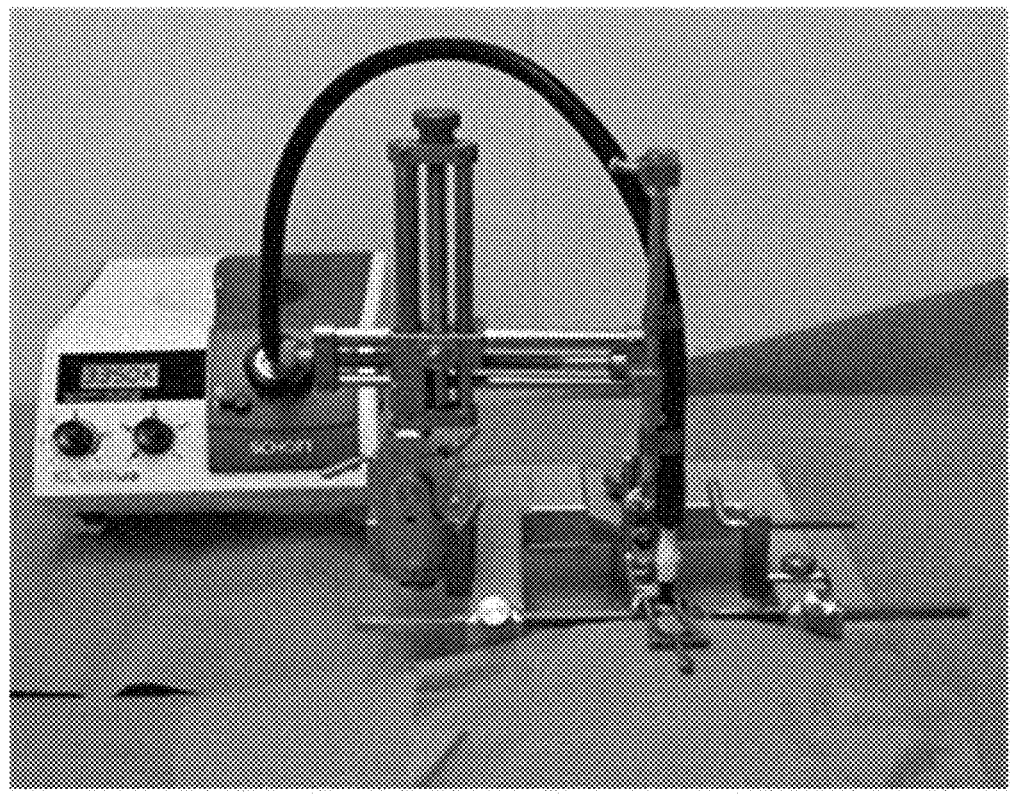
FIG. 9 is an image of a medical device designed to establish an animal stroke model using a small animal (e.g., a rat) according to one exemplary embodiment of the present invention.

Example 3: Evaluation of Efficiency of High-Intensity Electromagnetic Field Using Small Animal Stroke Model Example 3.1: Establishment of Small Animal Stroke Model To establish an animal stroke model, three-week-old SD rats (weighing 45 to 50 g) were used, and 0.1 cc/100 g (50 mg/kg) of Zoletil™ (250 mg/5 cc; Virbac) and 0.025 to 0.04/100 g (5 to 10 mg/kg) of Rompun 2% (Bayer) were mixed to prepare an anesthetic, and the anesthetic was intraperitoneally administered to anesthetize the rats. A method of establishing the animal stroke model was performed using a photochemical method, as follows. 300 μl of a systemic photoactive dye, Rose Bengal (10 mg/ml), was administered, and the rats' skulls were then irradiated with light beams to induce a stroke in the rats. FIG. 9 is an image of a medical device designed to establish an animal stroke model using the photochemical method.

Example 3.2: Stroke Therapeutic Effect of High-Intensity Electromagnetic Field Using Small Animal Model To evaluate an effect of the high-intensity electromagnetic field, rats were divided into four experimental groups: a first group (control) in which physiological saline (100 μl) was administered to a rat stroke model; a second group in which adult stem cells were administered to a rat stroke model (cell number: $1 \times 10^6$); a third group in which adult stem cells were administered to a rat stroke model and treated with low-intensity electromagnetic field (at 60 Hz and 1 mT for 60 min/day); and a fourth group in which adult stem cells were administered to a rat stroke model and treated with high-intensity electromagnetic field (at 60 Hz and 630 mT for 20 min/day).

A method of injecting the adult stem cells was performed, as follows:

A rat stroke model was established. After 24 hours, the adult stem cells were administered through a tail vein in the rat stroke model. The cells were added to 500 μl of physiological saline so that the concentration of the cells was adjusted to be $1 \times 10^6$ cells, and then slowly injected for 2 minutes. An electromagnetic field was placed over the skull of a rat whose brain was positioned in the rat stroke model so that the adult stem cells were treated with the electromagnetic field, and the treatment with the electromagnetic field was carried out daily for 20 minutes over 14 days after 24 hours of the cell administration.

After 14 days, the rat was euthanized, and tissue around the cerebral infarction was taken, and then subjected to Western blotting, hematoxylin & eosin (H&E) staining, and an immunohistochemical assay.

Figure 10:
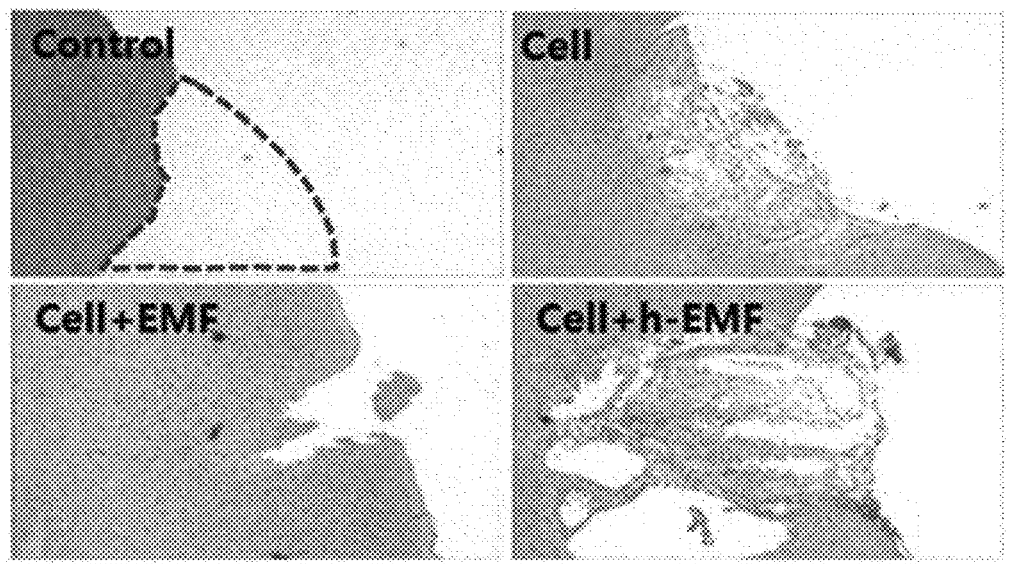
FIG. 10 shows hematoxylin & eosin (H&E) staining results of tissues after a small animal stroke model is established and adult stem cells are then injected and treated with a high-intensity electromagnetic field according to one exemplary embodiment of the present invention (Control: control group; Cell: an adult stem cell-administered group; Cell+EMF: an adult stem cell-administered/low-intensity electromagnetic field-treated group; and Cell+h-EMF: an adult stem cell-administered/high-intensity electromagnetic field-treated group).

FIG. 10 shows H&E staining results. It was revealed that a damaged part (dotted circle) was empty in the untreated group, a damaged part of the brain tissue was observed from the H/E staining results, and the tissues in the stoke-induced part were regenerated in the electromagnetic field-treated groups. There was no significant morphological difference between the experimental groups.

Figure 11:
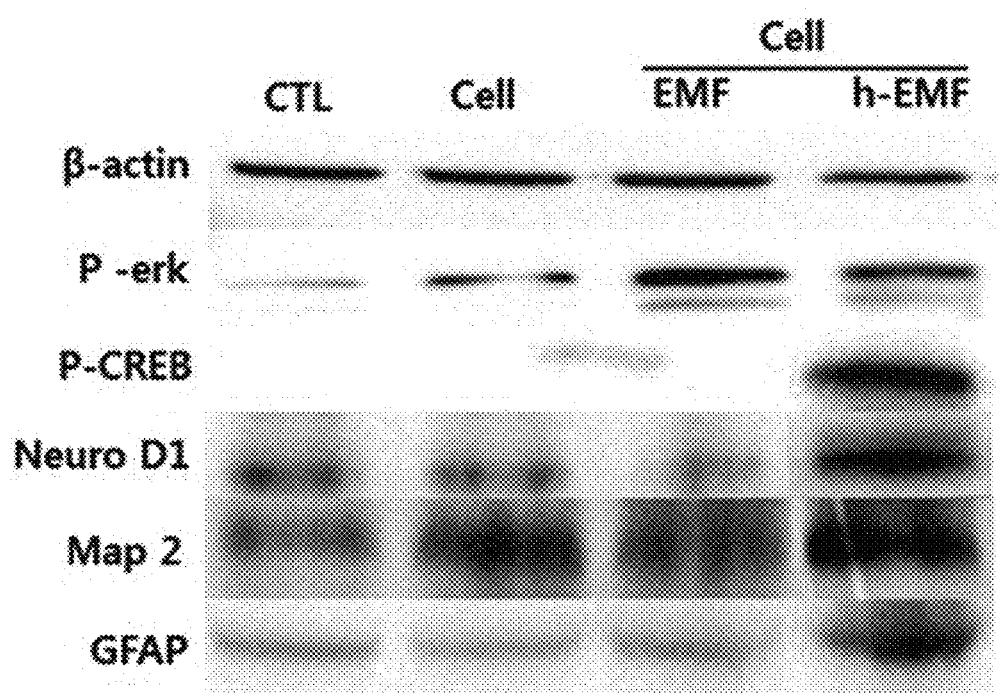
FIG. 11 shows results of comparing expression levels of neuron-associated proteins after a small animal stroke model is established and adult stem cells are then injected and treated with a high-intensity electromagnetic field according to one exemplary embodiment of the present invention (Control: control group; Cell: an adult stem cell-administered group, Cell+EMF: an adult stem cell-administered/low-intensity electromagnetic field-treated group, and Cell+h-EMF: an adult stem cell-administered/high-intensity electromagnetic field-treated group).

Also, FIG. 11 shows results of Western blotting carried out to check the expression of the neuronal differentiation-associated proteins in adult stem cells according to the frequencies of the electromagnetic field. It was revealed that the neuron-associated proteins p-ERK, p-CREB, MAP 2, and Neuro D1 were strongly expressed in the high-intensity electromagnetic field-treated group.

Further, to compare effects of induction of differentiation of the adult stem cells according to the treatment with the high-intensity/low-frequency electromagnetic field, the expression levels of MMP 1, Neuro D1, and NF-L were determined through immunohistochemical staining. The results are shown in FIGS. 12, 13 and 14. As shown in FIGS. 12, 13 and 14, it was revealed that the expression of the Neuro D1 and NF-L proteins increased in the high-intensity electromagnetic field-treated groups, compared to the untreated group in which the stem cells were not treated with the low-intensity electromagnetic field. It was observed that the expression of MMP-1 was significantly reduced in the h-EMF-treated group, and Neuro D1 and NF-L were strongly stained in the h-EMF-treated group, indicating that the nerve regeneration most actively occurred. That is, it could be seen that, since the proteins were strongly expressed in the adult stem cells cultured while being treated with an electromagnetic field having a frequency of 60 Hz frequency and a high intensity of 630 mT for 20 min/day, the electromagnetic field induced the neuronal differentiation of the adult stem cells.

Example 4: Evaluation of Cell Differentiation Efficiency According to Various Frequencies of High-Intensity Electromagnetic Field Example 4.1: Culturing of Mesenchymal Stem Cells Derived from Human Bone Marrow Human bone marrow-derived mesenchymal stem cells whose passage number was 2 were purchased from Lonza (Walkersville, Md.), put into an NH medium, and then centrifuged at 800 rpm for 5 minutes. A supernatant obtained by the centrifugation was discarded, and the remaining cells were again seeded in a 100 mm culture plate containing 10 ml of an NH medium, and then cultured in a $CO_2$ incubator maintained at a constant temperature of 37° C. while the medium was replaced with a fresh one every three days.

Example 4.2: Evaluation of Differentiation Ability of Mesenchymal Stem Cells According to Various Frequencies of High-Intensity Electromagnetic Field After the primary culturing, the medium was removed, and the cultured cells were washed with 10 ml of phosphate buffered saline (PBS) one or more times. 1 ml of a solution containing 0.05% (w/v) trypsin and 0.01% (w/v) EDTA was added to the washed cells, and the cells were treated at 37° C. for 5 minutes so that the cells were detached from the bottom of the culture plate to float in the solution. The cell solution was mixed with 15 ml of an NH medium containing 10% (v/v) FBS, and the mixture was then centrifuged at 800 rpm for 5 minutes to discard a supernatant and collect the cells. The collected cells were sub-cultured up to five times in a $CO_2$ incubator.

The cultured cells were seeded in a DMEM medium-containing 60 mm culture plate at a concentration of 0.25×$10^5$ cells/culture plate, and then cultured in a $CO_2$ incubator at 37° C. for 8 days while the medium was replaced with a fresh one every three days. In this case, the experimental groups were treated with a high-intensity electromagnetic field.

Figure 15:
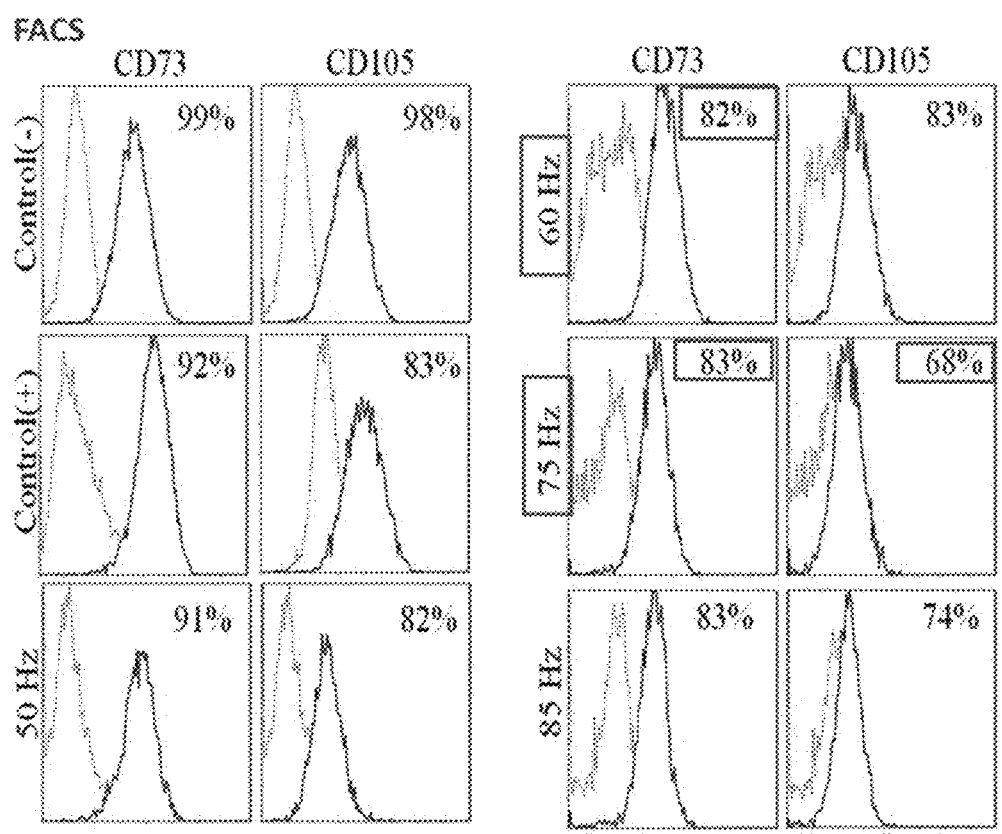
FIG. 15 shows fluorescence-activated cell sorting (FACS) results of tissues after neuronal differentiation of adult stem cells using a high-intensity electromagnetic field according to one exemplary embodiment of the present invention (C−: an untreated group using a growth medium; C+: an untreated group using a differentiation medium; and 50 Hz, 60 Hz, 75 Hz, and 85 Hz: treated with frequencies of the high-intensity electromagnetic field).

The treatment with the high-intensity electromagnetic field was performed once daily for 20 minutes over a culture period. When the treatment was performed, the 60 mm culture plate was placed over the high-intensity electromagnetic field, and the cells were then cultured for 7 days under the electromagnetic field having a frequency of 0 Hz (an untreated group), 50 Hz, 60 Hz, 75 Hz, and 85 Hz. The cells were cultured in a DMEM medium supplemented with 5% FBS, 10 ng/ml EGF, and 10 μM Forskolin. After the culturing, a FACS assay was performed to check neuronal differentiation efficiency at 0 Hz (an untreated group), 50 Hz, 60 Hz, 75 Hz, and 85 Hz. The results are shown in FIG. 15.

The cultured cells of each experimental group were collected, and subjected to a FACS assay. As a result, it was confirmed that the expression of CD105 and CD73 at 60 Hz and 75 Hz was reduced, as shown in FIG. 15, indicating that the mesenchymal stem cells were differentiated.

Figure 16:
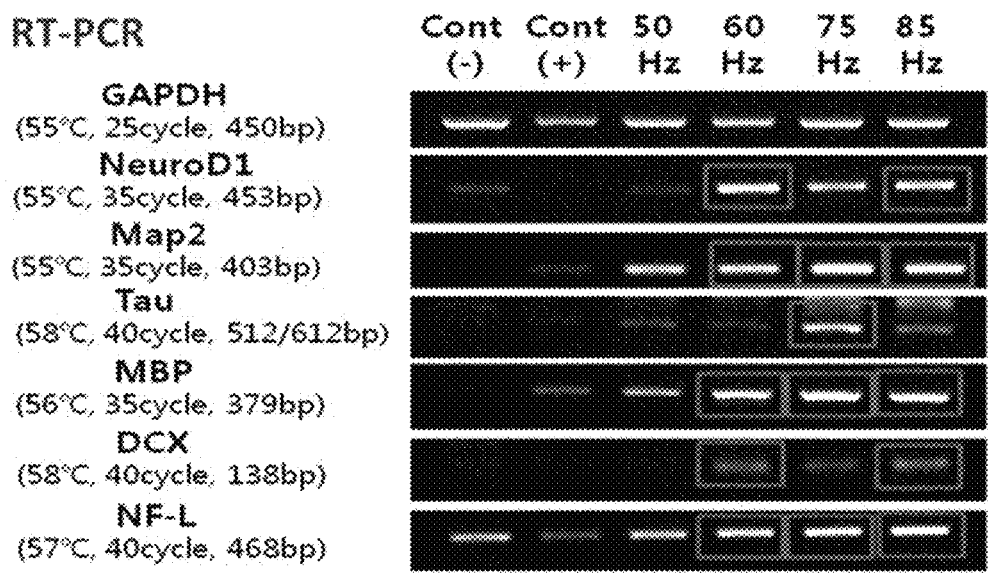
FIG. 16 shows results of comparing expression levels of neuron-associated mRNAs after neuronal differentiation of adult stem cells using a high-intensity electromagnetic field according to one exemplary embodiment of the present invention (C−: an untreated group using a growth medium; C+: an untreated group using a differentiation medium; and 50 Hz, 60 Hz, 75 Hz, and 85 Hz: treated with frequencies of the high-intensity electromagnetic field).

After the culturing, the cells were collected to determine mRNA expression levels of the nerve cell-associated factors Neuro D1, Map2, Tau, MBP, DCX, and NF-L. As shown in FIG. 16, an amount of the nerve cell-associated proteins increased in the human mesenchymal stem cells cultured using the high-intensity electromagnetic field. In particular, the mRNAs of the neuron-associated factors were expressed to the highest level in the mesenchymal stem cells cultured under the electromagnetic field having a frequency of 60 Hz, 75 Hz and 80 Hz (85 Hz???).

Figure 17:
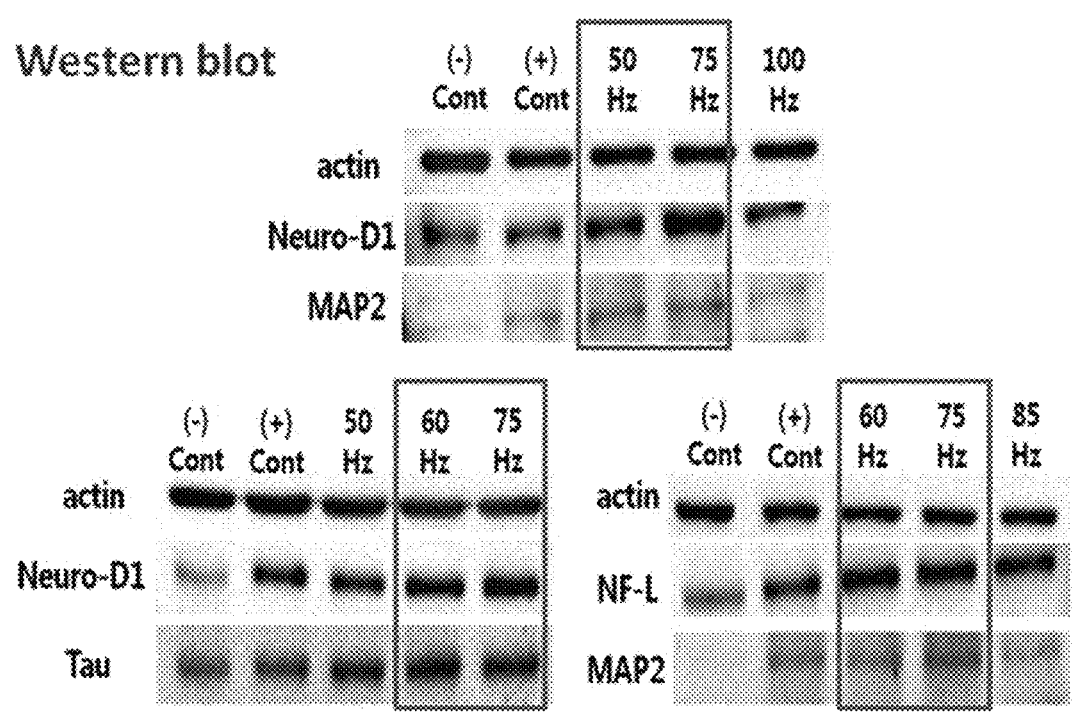
FIG. 17 shows results of comparing expression levels of neuron-associated proteins after neuronal differentiation of adult stem cells using a high-intensity electromagnetic field according to one exemplary embodiment of the present invention (C−: an untreated group using a growth medium; C+: an untreated group using a differentiation medium; and 50 Hz, 60 Hz, 75 Hz, and 85 Hz: treated with frequencies of the high-intensity electromagnetic field)

To compare the expression levels of the neuron-associated proteins, the mesenchymal stem cells were cultured, collected, and then subjected to Western blotting. The results are shown in FIG. 17. The neuron-associated proteins Neuro D1, Tau, and Map2 were expressed to the highest level in the mesenchymal stem cells cultured under the electromagnetic field having a frequency of 60 Hz and 75 Hz.

Figure 18:
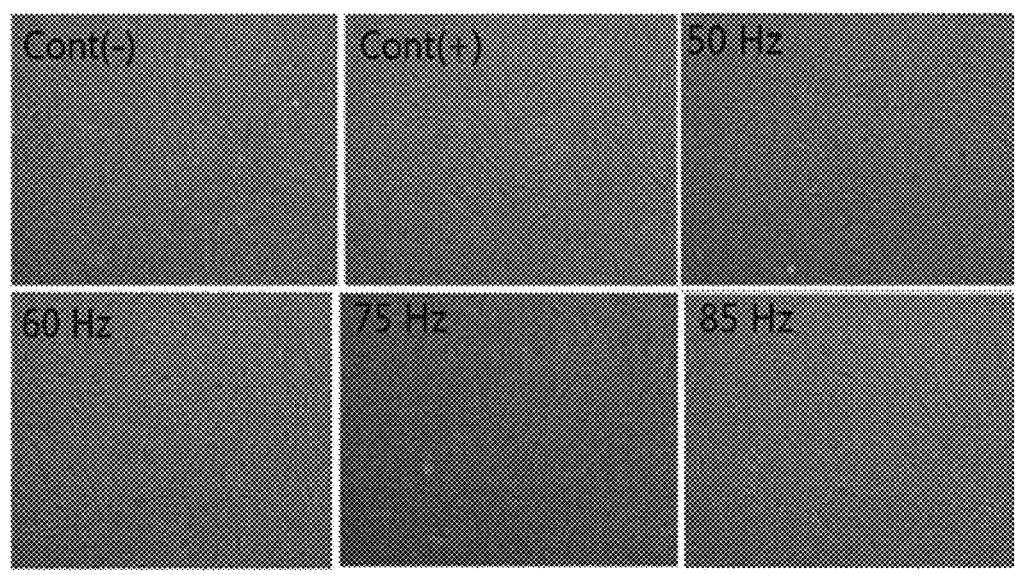
FIG. 18 is an image obtained by observing morphological changes of bone marrow-derived mesenchymal stem cells after the mesenchymal stem cells were treated with a high-intensity electromagnetic field according to one exemplary embodiment of the present invention (100×; Cont−: an untreated group using a growth medium; Cont+: an untreated group using a differentiation medium; and 50 Hz, 60 Hz, 75 Hz, 85 Hz: treated with frequencies of the high-intensity electromagnetic field).
Figure 19:
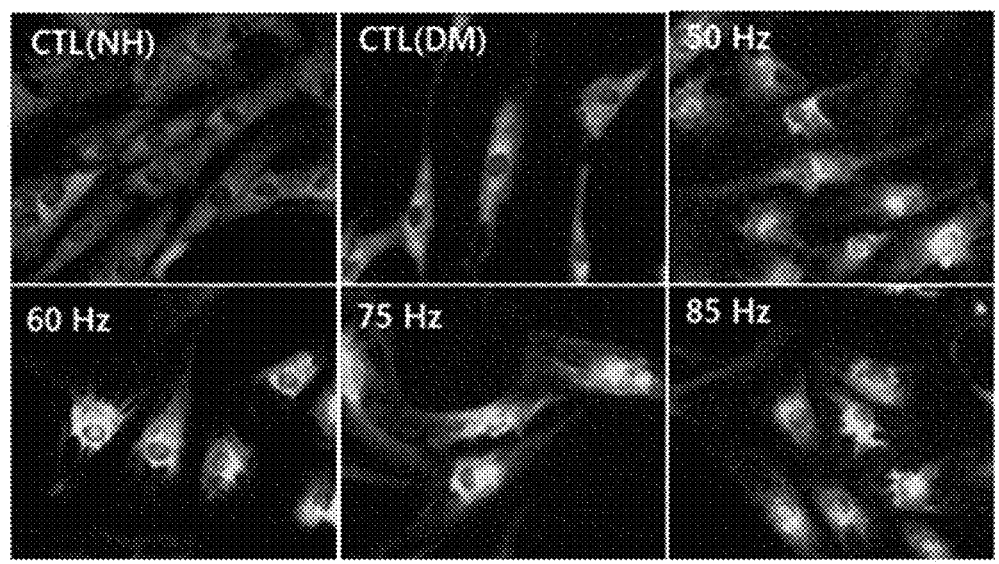
FIG. 19 shows fluorescence staining results of tissues obtained by observing neurofilaments as a neuronal differentiation-associated factor after treatment with a high-intensity electromagnetic field according to one exemplary embodiment of the present invention (CTL: an untreated group; and 50 Hz, 60 Hz, 75 Hz, and 85 Hz: treated with frequencies of the high-intensity electromagnetic field)
Figure 20A:
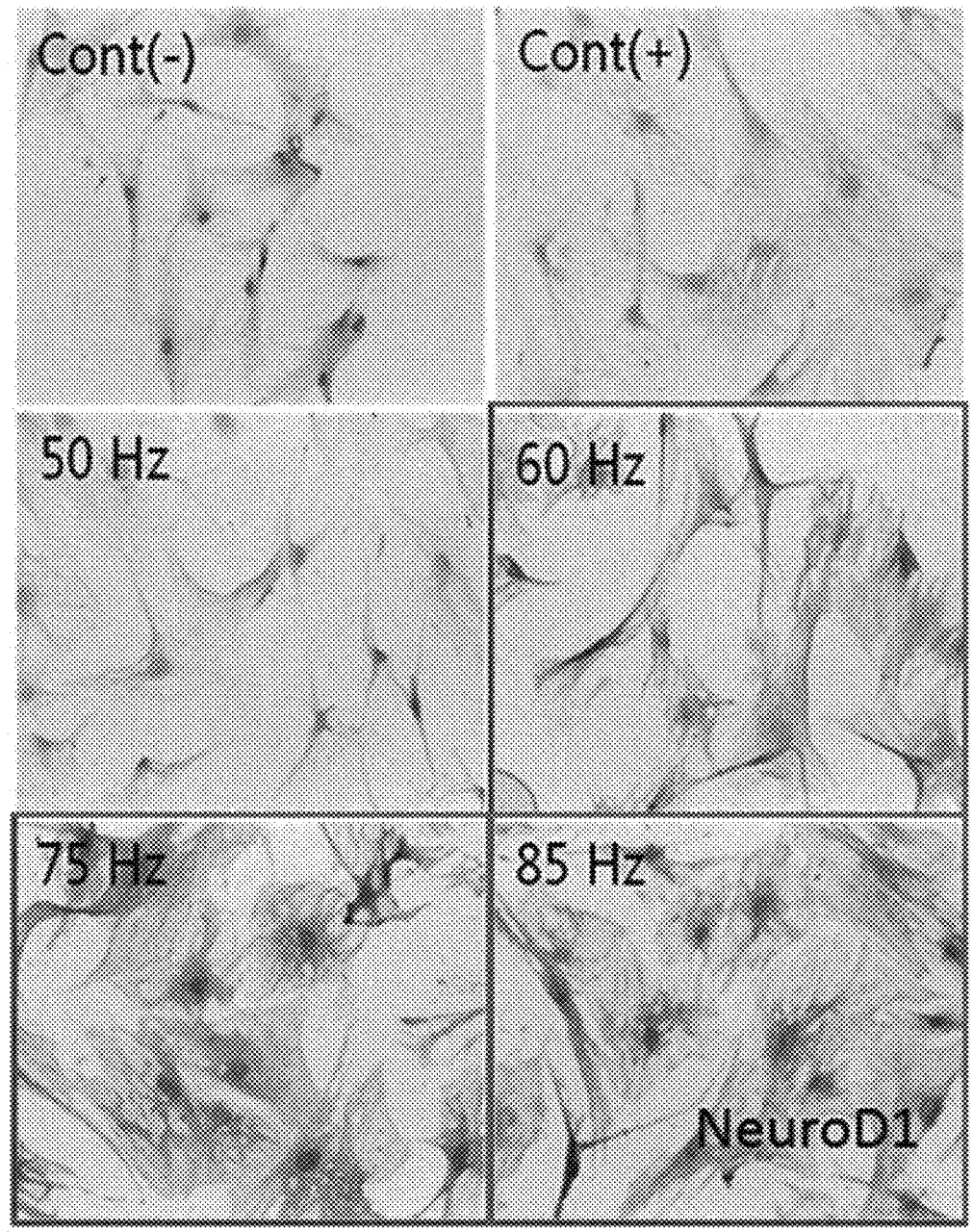
FIG. 20 shows immunostaining results of comparing expression levels of neuronal differentiation-associated factors Neuro D1 (FIG. 20A) and MAP2 (FIG. 20B) after treatment with a high-intensity electromagnetic field according to one exemplary embodiment of the present invention (Cont (−): an untreated group using a growth medium; Cont (+): an untreated group using a differentiation medium; and 50 Hz, 60 Hz, 75 Hz, and 85 Hz: treated with frequencies of the high-intensity electromagnetic field).
Figure 20B:
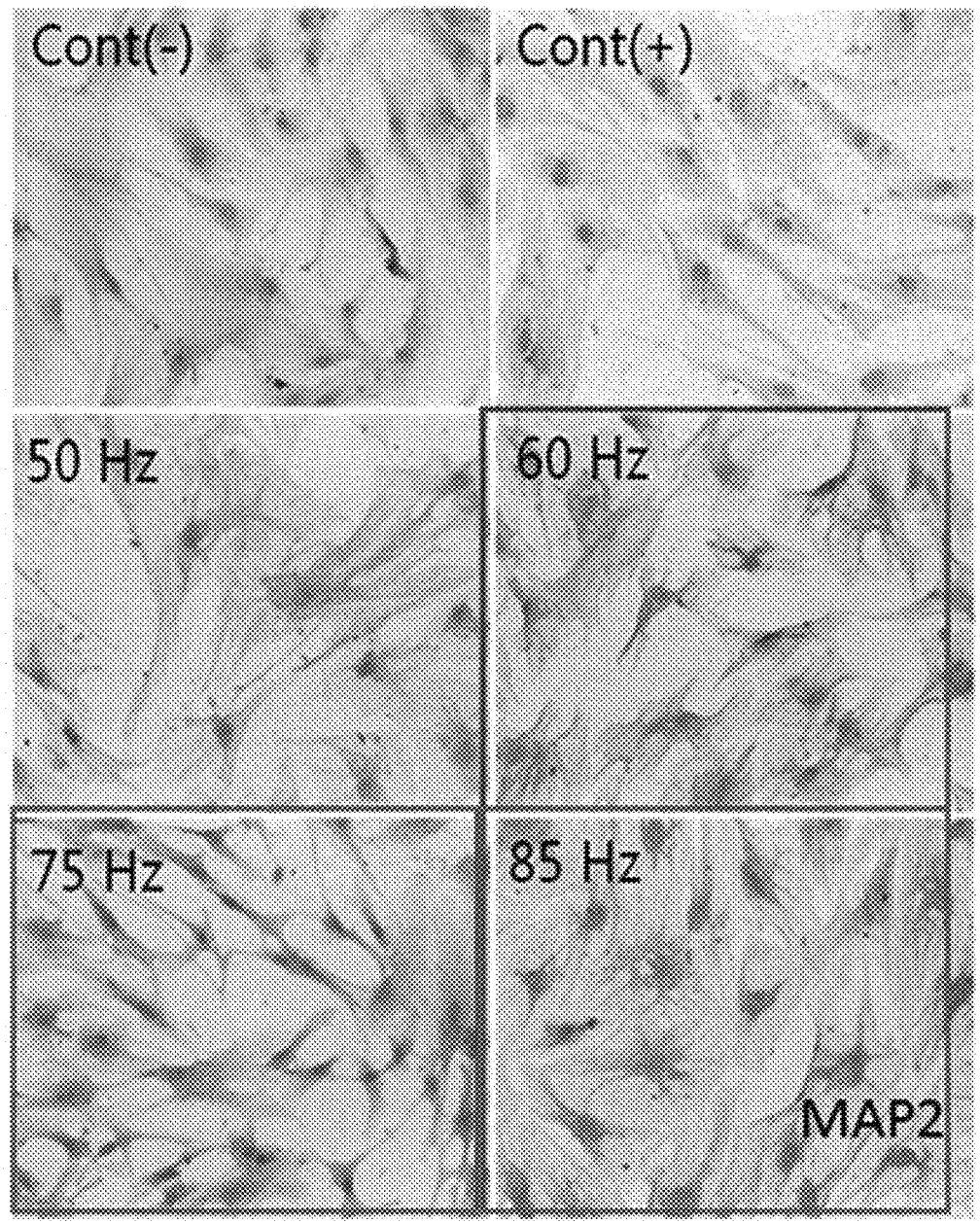
Figure 21A:
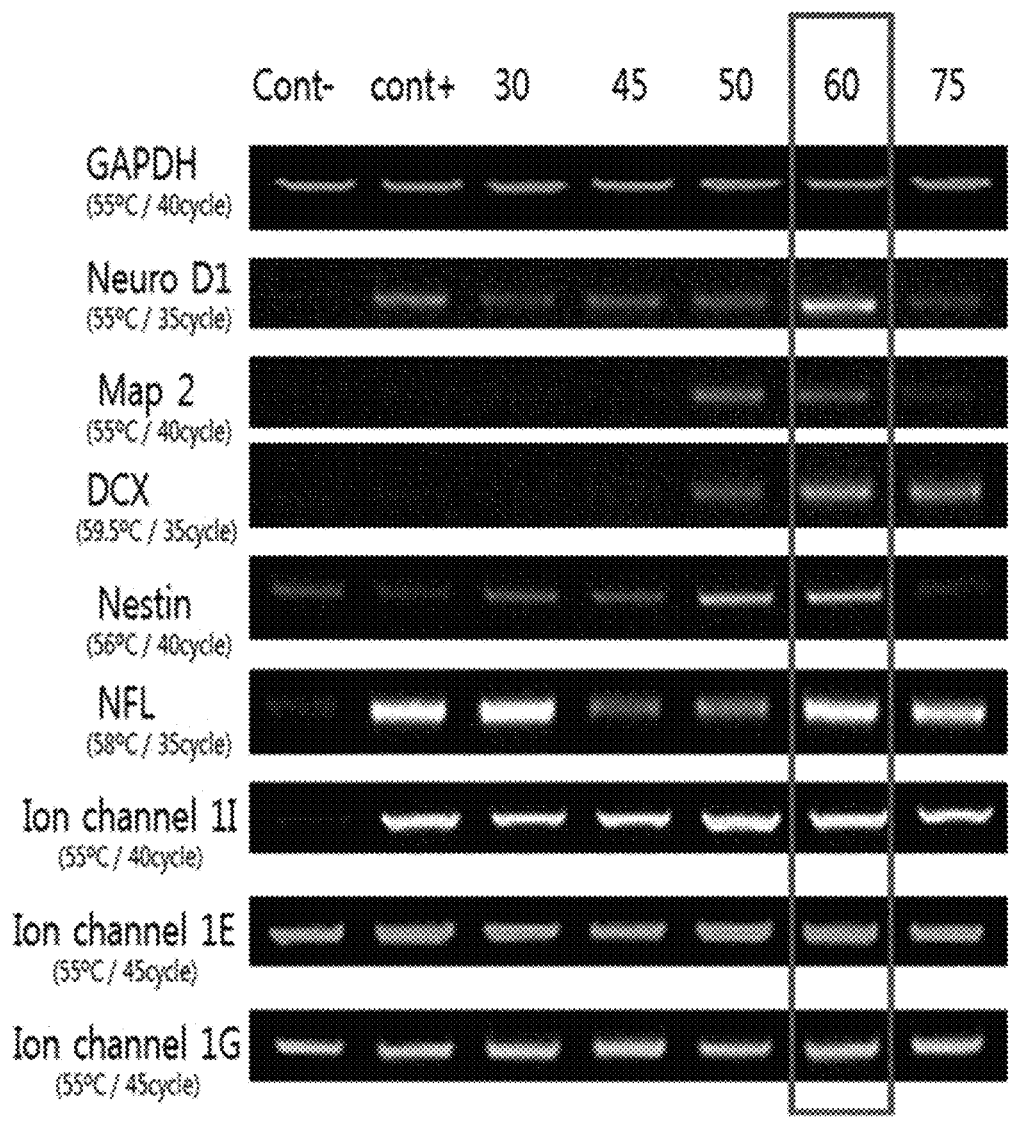
FIGS. 21A and 21B show results of comparing mRNA expression levels of Neuro D1, MAP2, DCX, Nestin, and NFL as neuronal differentiation-associated factors and mRNA expression levels of ion channels 1I, 1E and 1G as ion channel-associated factors after treatment with a high-intensity electromagnetic field according to one exemplary embodiment of the present invention (Cont−: an untreated group using a growth medium; Cont+: an untreated group using a differentiation medium; and 30 Hz, 45 Hz, 50 Hz, 60 Hz, and 75 Hz: treated with frequencies of the high-intensity electromagnetic field)
Figure 21B:
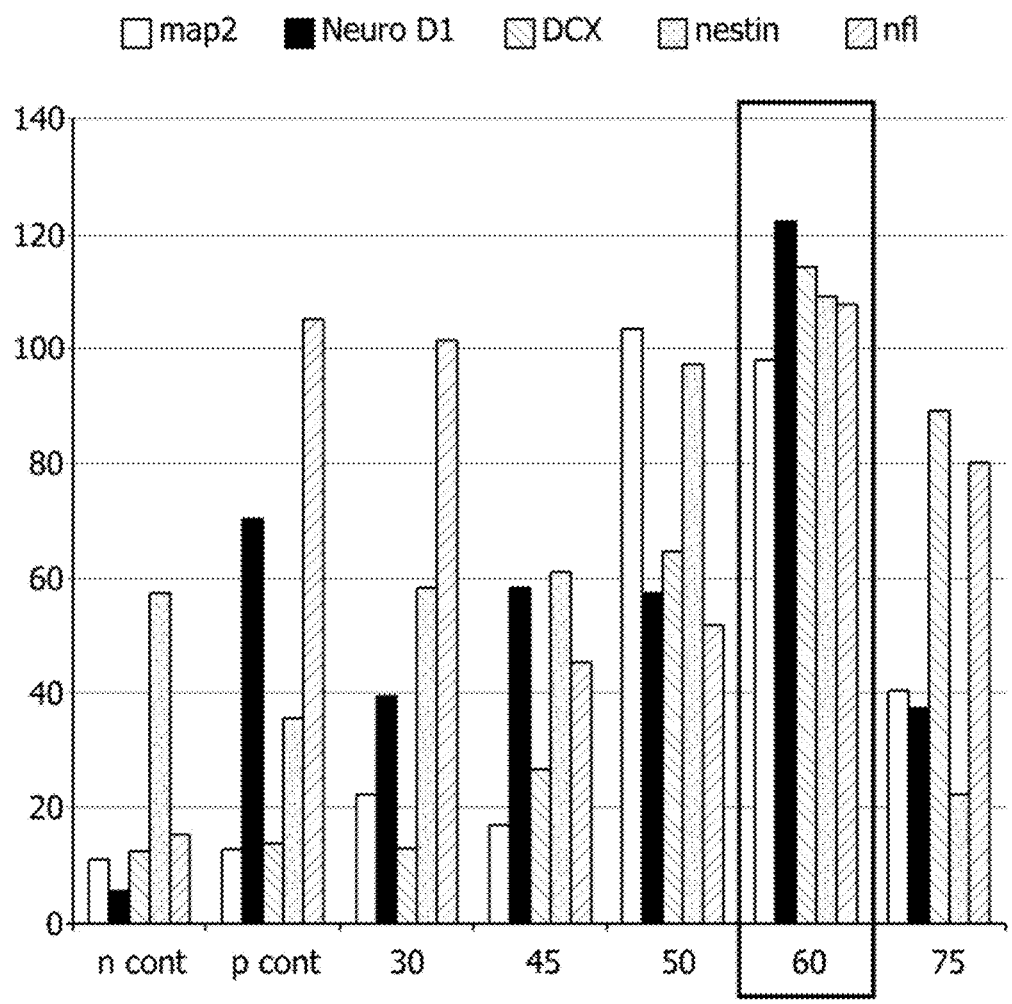

The mesenchymal stem cells were cultured under a high-intensity electromagnetic field having a frequency of 50 Hz, 60 Hz, 75 Hz, and 85 Hz, and then observed under an optical microscope to determine a morphological change of the bone marrow-derived cells. The results are shown in FIG. 18.

Example 5: Evaluation of Efficiency of High-Intensity Electromagnetic Field Using Mouse Stroke Model

Example 5.1: Evaluation of Effect of High-Intensity Electromagnetic Field on Mouse Stroke Model To establish an animal stroke model, six-week-old C57BL/6N mice (weighing 20 to 22 g) were used, and 0.1 cc/100 g (50 mg/kg) of Zoletil (250 mg/5 cc; Virbac) and 0.025 to 0.04/100 g (5 to 10 mg/kg) of Rompun 2% (Bayer) were mixed to prepare an anesthetic, and the anesthetic was intraperitoneally administered to anesthetize the rats. A method of establishing the animal stroke model was performed using a photochemical method, as follows. 100 μl of a systemic photoactive dye, Rose Bengal (10 mg/ml), was administered, and the mice' skulls were then irradiated with light beams (KL 1,500 LCD (SCHOTT); a wavelength of 532 nm) for 15 minutes to induce a stroke in the mice.

To select mice used for experiments, before a mouse stroke model was established, a Rotarod test (20 rpm) was carried out on all the mice for one week to select the mice whose motor ability was maintained for 80 seconds. After 3 days of stroke occurrence, the Rotarod test was again carried out to select only the mice which fell from a rotarod within 40 seconds, and the selected mice were used in experiments.

To evaluate a nerve regeneration effect of the high-intensity electromagnetic field using a mouse stroke model, the mice were divided into three experimental groups: a first group (negative control) in which physiological saline was administered to a mouse stroke model; a second group in which adult stem cells were administered to a mouse stroke model (cell number: 1×$10^5$; control group), and a third group in which adult stem cells were administered to a mouse stroke model and then treated with a high-intensity electromagnetic field (at 60 Hz and 500 mT for 15 min/day).

A method of treating the adult stem cells with the high-intensity electromagnetic field was as follows. A mouse was put into a 50 cc syringe to be fixed therein, and positioned on a high-intensity electromagnetic coil so that the head of the mouse faced inward, and the adult stem cells were then treated with the high-intensity electromagnetic field. The treatment with the high-intensity electromagnetic field was performed for 2 weeks.

Example 5.2: Evaluation of Motor Recovery Ability of Stroke Mouse

A Rotarod test was performed to evaluate motor recovery abilities of the stroke mice prepared in Example 5.1.

Figure 22A:
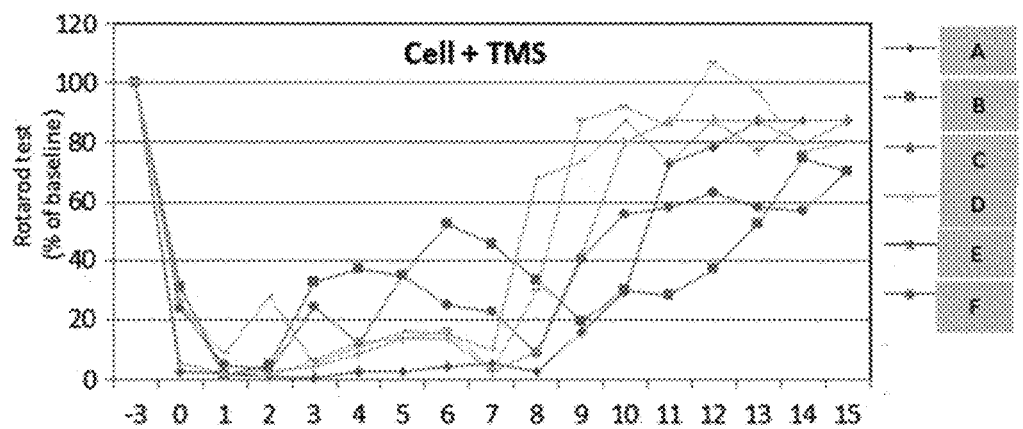
FIG. 22 shows results of evaluating motor recovery abilities (Rotarod) of experimental groups in which an animal stroke model is established and adult stem cells are then injected and treated with a high-intensity electromagnetic field according to one exemplary embodiment of the present invention (Control: an untreated group in FIG. 22C; Cell: a cell-transplanted group in FIG. 22B; and Cell+TMS: a group in which stem cells are treated with the high-intensity electromagnetic field after cell transplantation in FIG. 22A)
Figure 22B:
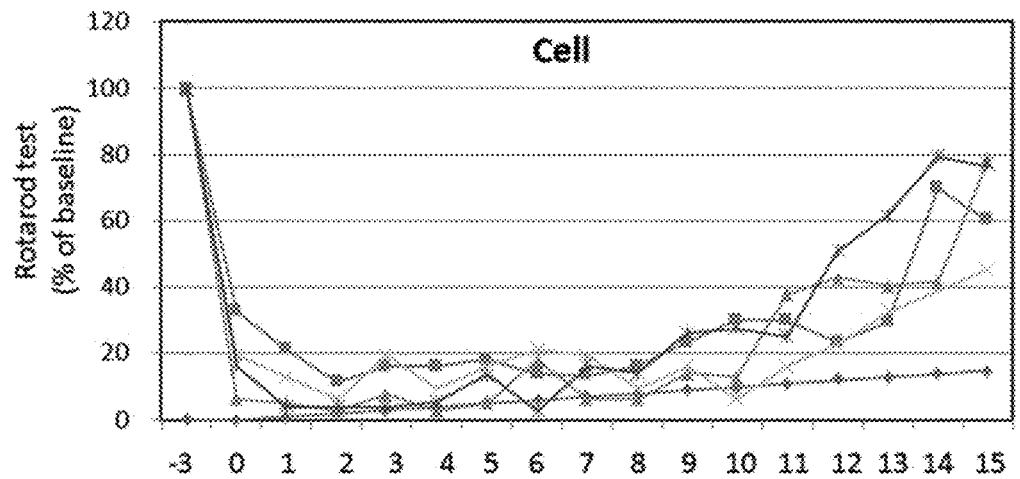
Figure 22C:
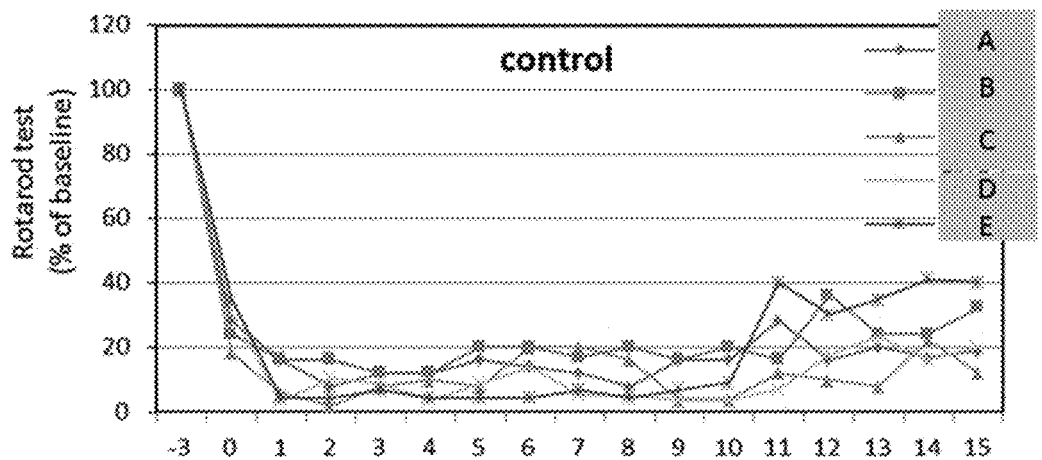

FIGS. 22A to 22C show results of evaluating motor recovery abilities (Rotarod) of the stroke mice in an untreated group (negative control), a cell-transplanted group (Cell as the control group), and a group in which the stem cells are treated with a high-intensity electromagnetic field after cell transplantation (Cell+TMS) for two weeks, respectively. It was revealed that the motor recovery abilities were improved in the control group and the high-intensity electromagnetic field-treated group, compared to the untreated group. In particular, it can be seen that the rapid recovery abilities were observed after 10 days of the treatment with the high-intensity electromagnetic field.

Example 5.3: Histological Examination and Protein Analysis after Treatment of Mouse Stroke Model with High-Intensity Electromagnetic Field After 2 weeks, the mice prepared in Example 5.1 were euthanized, and tissues around stroke lesions were taken, and then subjected to hematoxylin & eosin staining and an immunohistochemical assay.

Figure 24:
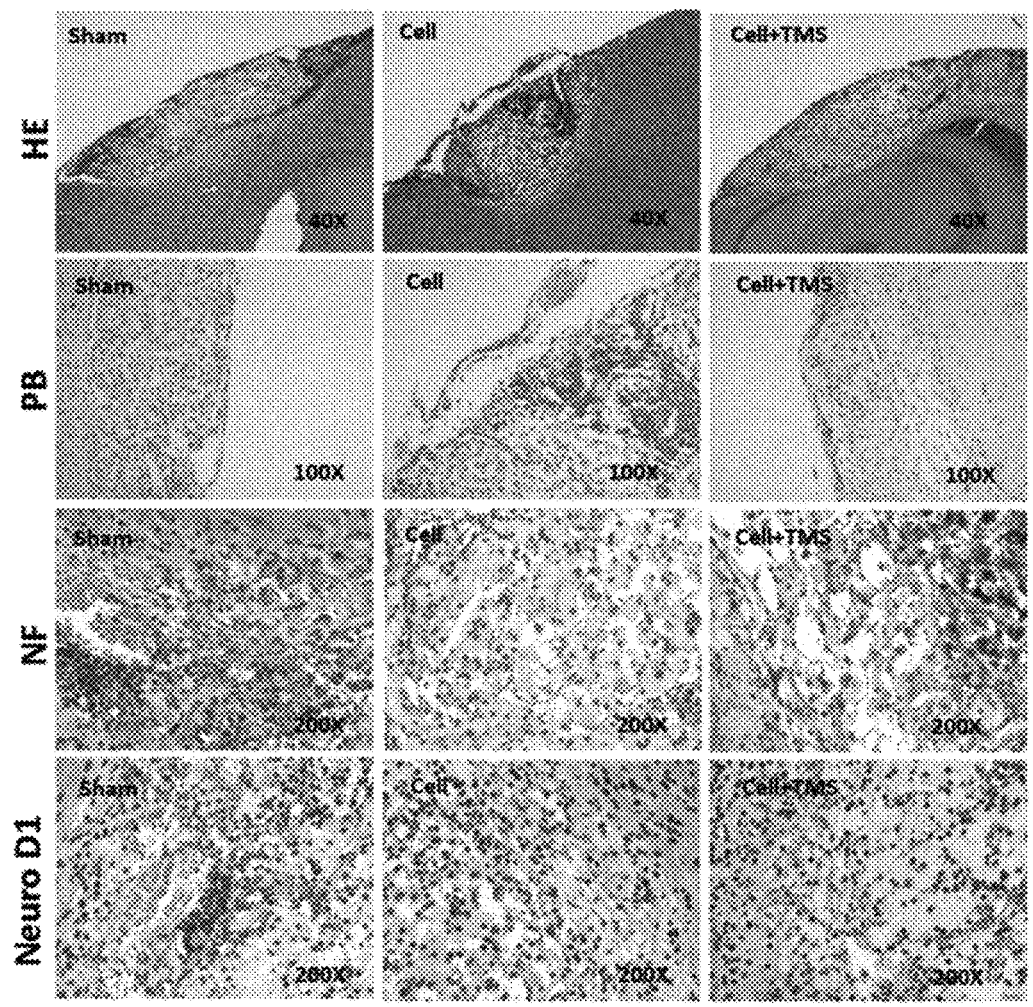
FIG. 24 shows results obtained by biopsying tissues and staining the tissues with hematoxylin & eosin, Prussian blue, NF200, Neuro D1 stains after a small animal stroke model is established and adult stem cells are then injected and treated with a high-intensity electromagnetic field according to one exemplary embodiment of the present invention (Sham: an untreated group; Cell: a cell-transplanted group; and Cell+TMS: a group in which stem cells are treated with the high-intensity electromagnetic field after cell transplantation).

FIG. 24 shows results of biopsying tissues of the stroke mice in an untreated group (negative control), a cell-transplanted group (control group), and a group in which the stem cells are treated with a high-intensity electromagnetic field after cell transplantation, and staining the tissues with H&E stains, Prussian blue, NF200, and Neuro D1 stains. In the untreated group, a necrotic part of the stroke lesion was removed to form a cavity (H&E staining). The migration of the injected cells was observed using Prussian blue. As a result, it could be seen that the magnetic nanoparticles stained blue around the stroke lesion were observed, indicating that the cells had migrated to the stroke lesion (Prussian blue). To observe regeneration of tissues around the stroke lesion, an NF200 protein was analyzed. As a result, it was observed that the tissues of the mice in the experimental groups treated with the high-intensity electromagnetic field after the cell transplantation were stained darkest brown (NF200), indicating that the tissue regeneration most actively occurred. It was revealed that Neuro D1 was expressed at the weakest level in the negative control, and increasingly expressed in the cell-transplanted group (control group) and the group in which the stem cells were treated with the high-intensity electromagnetic field after cell transplantation.

Figure 23A:
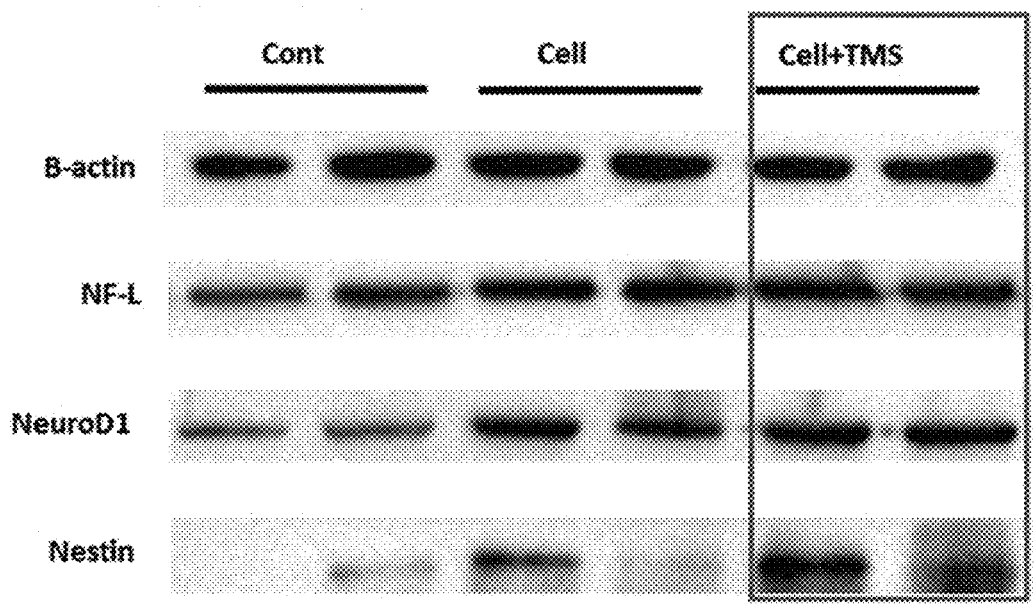
FIGS. 23A and 23B show results of comparing expression levels of neuron-associated proteins after a mouse stroke model is established and adult stem cells are then injected and treated with a high-intensity electromagnetic field according to one exemplary embodiment of the present invention (Cont: an untreated group; Cell: a cell-transplanted group; and Cell+TMS: a group in which stem cells are treated with the high-intensity electromagnetic field after cell transplantation)
Figure 23B:
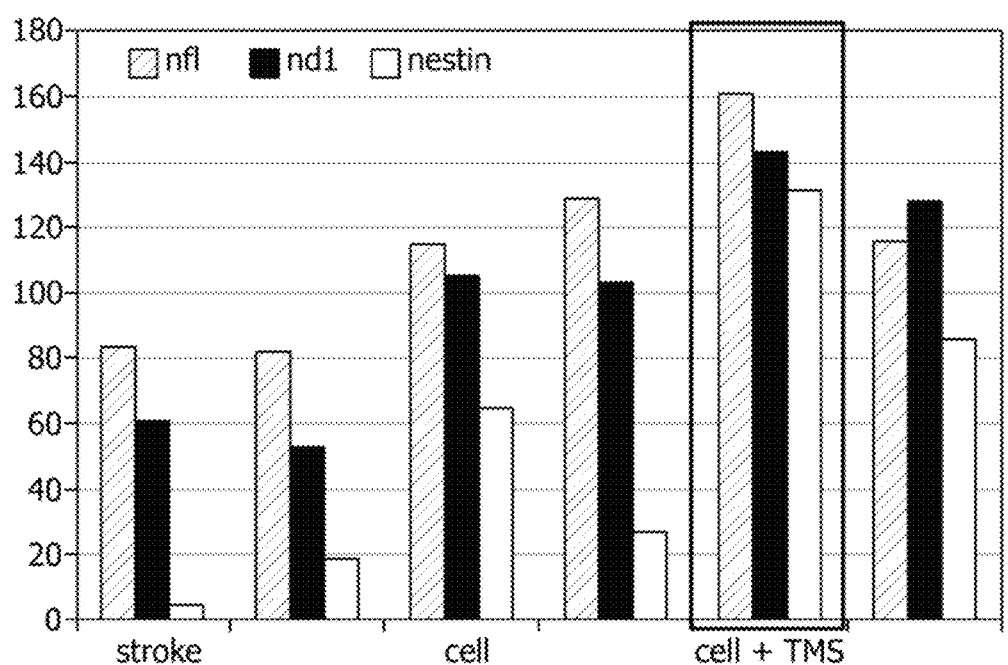

FIGS. 23A and 23B show results of biopsying tissues of the stroke mice in an untreated group (negative control), a cell-transplanted group (control group), and a group in which the stem cells are treated with a high-intensity electromagnetic field after cell transplantation, isolating proteins from the tissues and subjecting the proteins to Western blotting. After the occurrence of a stroke, the cells were injected, and treated with the high-intensity electromagnetic field. As a result, it was revealed that the expression of NFL, Neuro D1 and Nestin increased. That is, the neuronal proteins were most strongly expressed in the animal stroke model, and thus it could be seen that the regeneration of the damaged nerves was actively promoted when the damaged nerves were treated with the high-intensity electromagnetic field (with 60 Hz and 500 mT) once a day for 15 minutes.

The invention claimed is:

1. A method of differentiating mesenchymal stem cells or adult stem cells into nerve cells, comprising:

treating the mesenchymal stem cells or the adult stem cells under culturing in DMEM medium with an electromagnetic field having a high intensity of 100 to 1,500 mT and a frequency of 1 to 100 Hz for 5 to 30 min/day over 3 to 15 days wherein said mesenchymal stem cells or adult stem cells differentiate into nerve cells.

2. The method of claim 1, wherein the nerve cells comprise astrocytes or oligodendrocytes.

3. The method of claim 1, wherein the mesenchymal stem cells are derived from bone marrow, adipose tissue, or an umbilical cord.

4. The method of claim 1, wherein the adult stem cells comprise dental pulp stem cells or neural progenitor cells.

5. A method of differentiating mesenchymal stem cells or adult stem cells into nerve cells, comprising:

injecting the mesenchymal stem cells or the adult stem cells into a subject; and treating the mesenchymal stem cells or the adult stem cells with an electromagnetic field having a high intensity of 100 to 1,500 mT and a frequency of 1 to 100 Hz for 5 to 30 min/day over 3 to 15 days wherein said mesenchymal stem cells or adult stem cells differentiate into nerve cells.

6. The method of claim 5, wherein the nerve cells comprise astrocytes or oligodendrocytes.

7. The method of claim 5, wherein the mesenchymal stem cells are derived from bone marrow, adipose tissue, or an umbilical cord.

8. The method of claim 5, wherein the adult stem cells comprise dental pulp stem cells or neural progenitor cells.

* * * * *